United States Patent [19]
Lanpher et al.

[11] Patent Number: 5,333,106
[45] Date of Patent: Jul. 26, 1994

[54] APPARATUS AND VISUAL DISPLAY METHOD FOR TRAINING IN THE POWER USE OF AEROSOL PHARMACEUTICAL INHALERS

[75] Inventors: Ted W. Lanpher, Atherton, Calif.; Gregory B. Lanpher, York, Pa.; David J. Mishelevich, Cupertino; Steven H. Minar, El Granada, both of Calif.

[73] Assignee: Circadian, Inc., San Jose, Calif.

[21] Appl. No.: 958,868

[22] Filed: Oct. 9, 1992

[51] Int. Cl.$^5$ ...................... G06F 15/00; A61M 15/00
[52] U.S. Cl. .......................... 364/413.01; 128/200.12; 128/200.23; 128/725
[58] Field of Search ...................... 364/413.01, 413.02, 364/413.04; 428/200.12, 200.23, 200.17, 725, 726, 727; 73/23.22

[56] References Cited

U.S. PATENT DOCUMENTS

| | | | |
|---|---|---|---|
| 4,984,158 | 1/1991 | Hillsman | 364/413.04 |
| 5,005,582 | 4/1991 | Serikov et al. | 128/691 |
| 5,167,506 | 12/1992 | Kilis et al. | 434/262 |

Primary Examiner—Roy N. Envall, Jr.
Assistant Examiner—Khai Tran
Attorney, Agent, or Firm—Wilson, Sonsini, Goodrich & Rosati

[57] ABSTRACT

An apparatus for interactive training of a patient in the use of an aerosol inhaler includes a feedback display based upon air flow versus volume data in order to train patients to use a proper sequence of inhalation steps to insure maximum delivery of an aerosol pharmaceutical to target sites in the lungs. Flow and volume data are displayed to provide the patient and physician with a real-time, interactive representation of the inhalation process. Visual feedback to the patient includes a portrayal of the lungs which may be either three dimensional or an outline form in addition to or instead of an X-Y display. An important element of visual feedback is the portrayal of the distribution of representative droplets of aerosol medication in various stages of inhalation and breath holding. Thus, the patient is provided with meaningful feedback representative of the actual distribution of aerosol medication. The real-time representation of the delivery of medication to the lungs enables a patient to derive a maximum therapeutic benefit from pharmaceuticals which are administered through inhalation. The improved feedback also enables a patient to learn proper inhalation techniques which enable therapeutic agents to be such as aerosol glucocorticoids to be delivered directly to target sites in the lungs thereby bypassing the digestive system and obviating adverse side effects. The improved visual feedback to the patient representing the actual distribution of inhaled aerosol in the lungs conveys a conceptual understanding of the proper inhalation process and greatly increases the likelihood that a patient will learn and retain the correct inhalation technique.

21 Claims, 13 Drawing Sheets

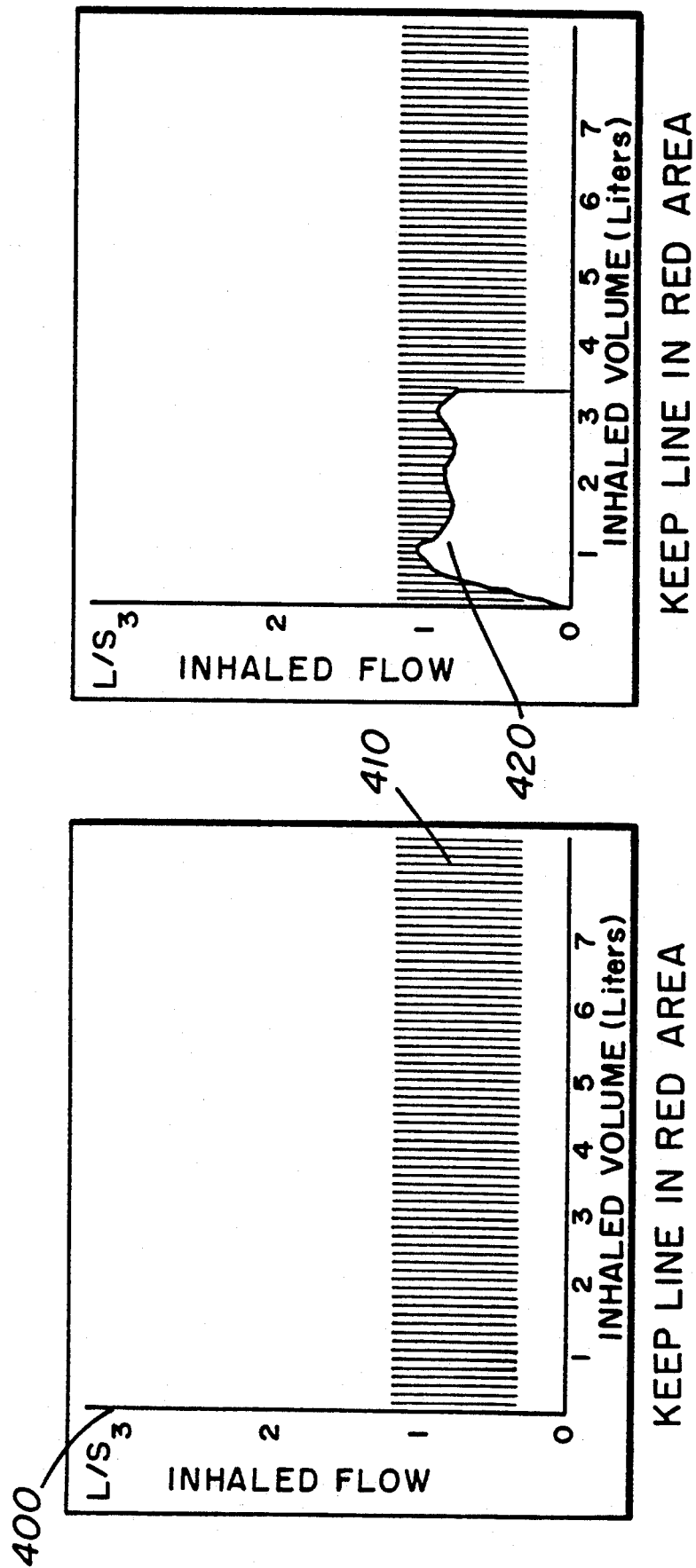

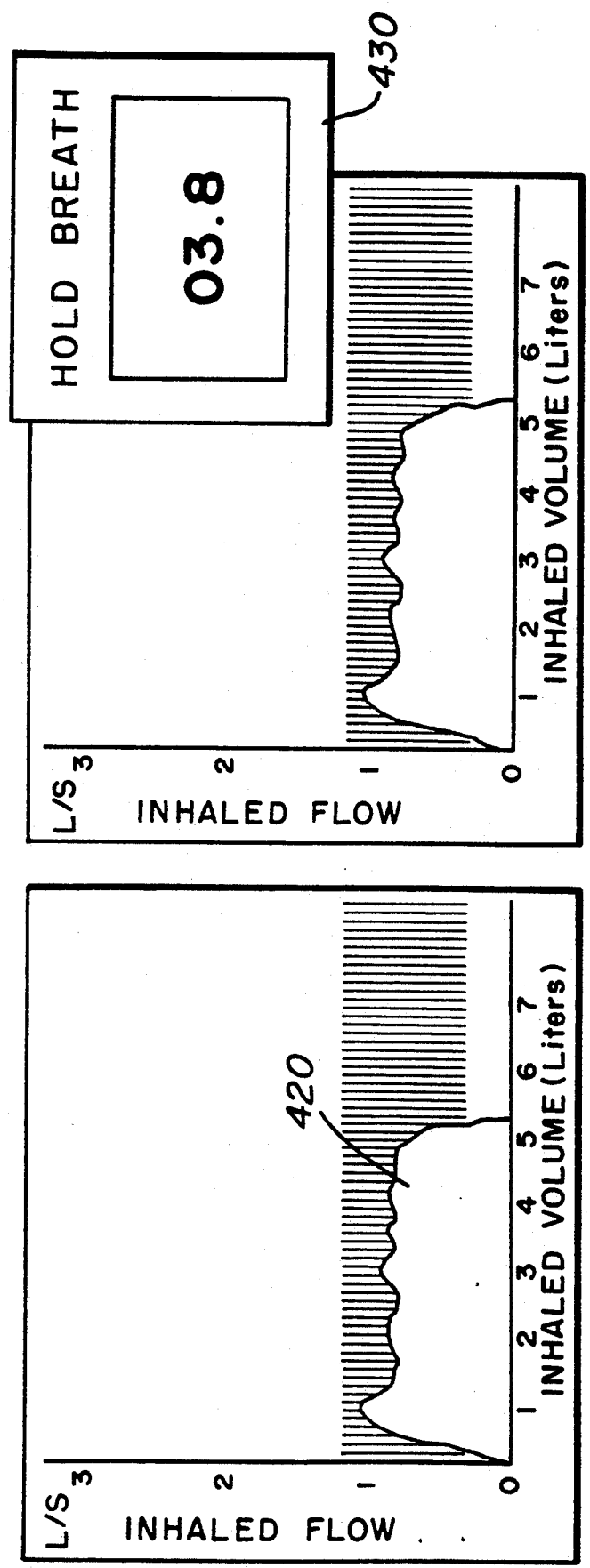

SCORING MECHANISM

CASE A
SCORE 80%

CASE B
SCORE 60%

CASE C
SCORE 20%

Volume inhaled at Target Rate

Volume inhaled above Target Rate

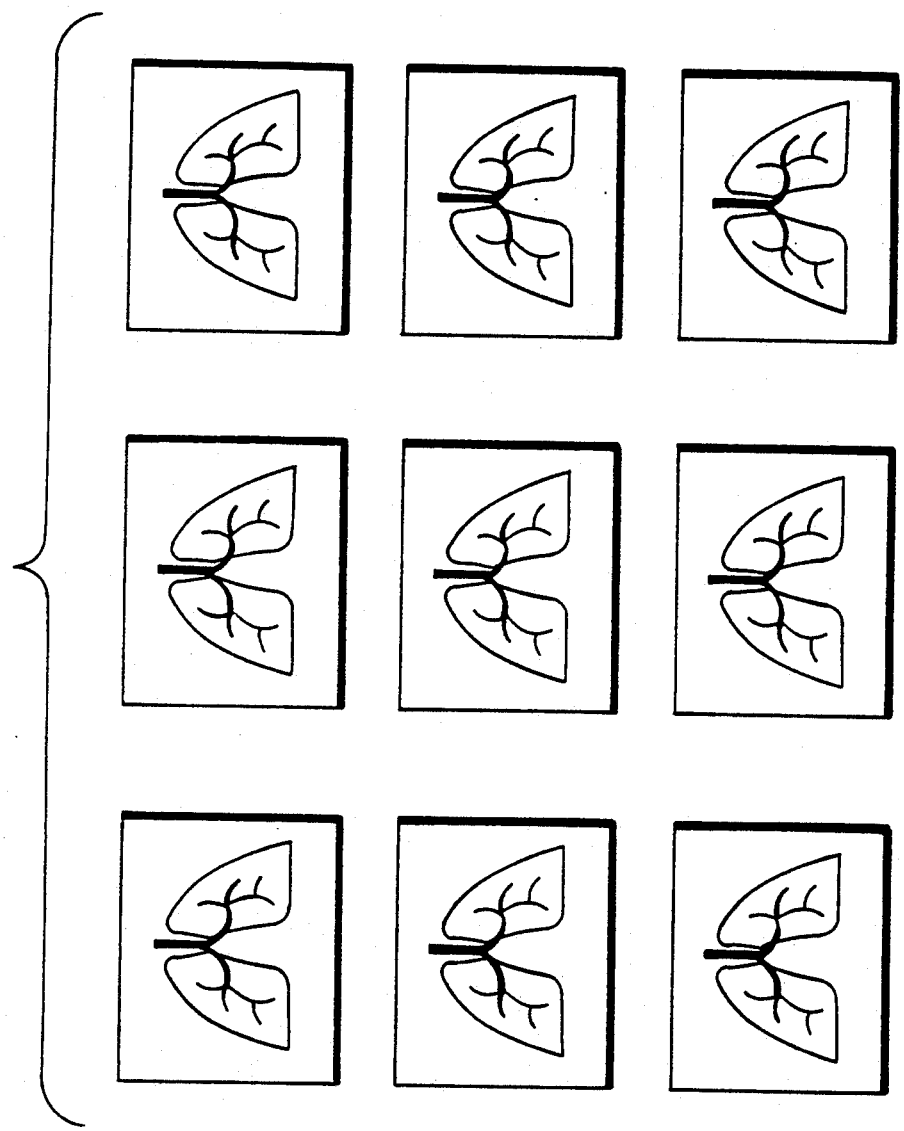
FIG. 7: TWO-DIMENSIONAL CEL MATRIX

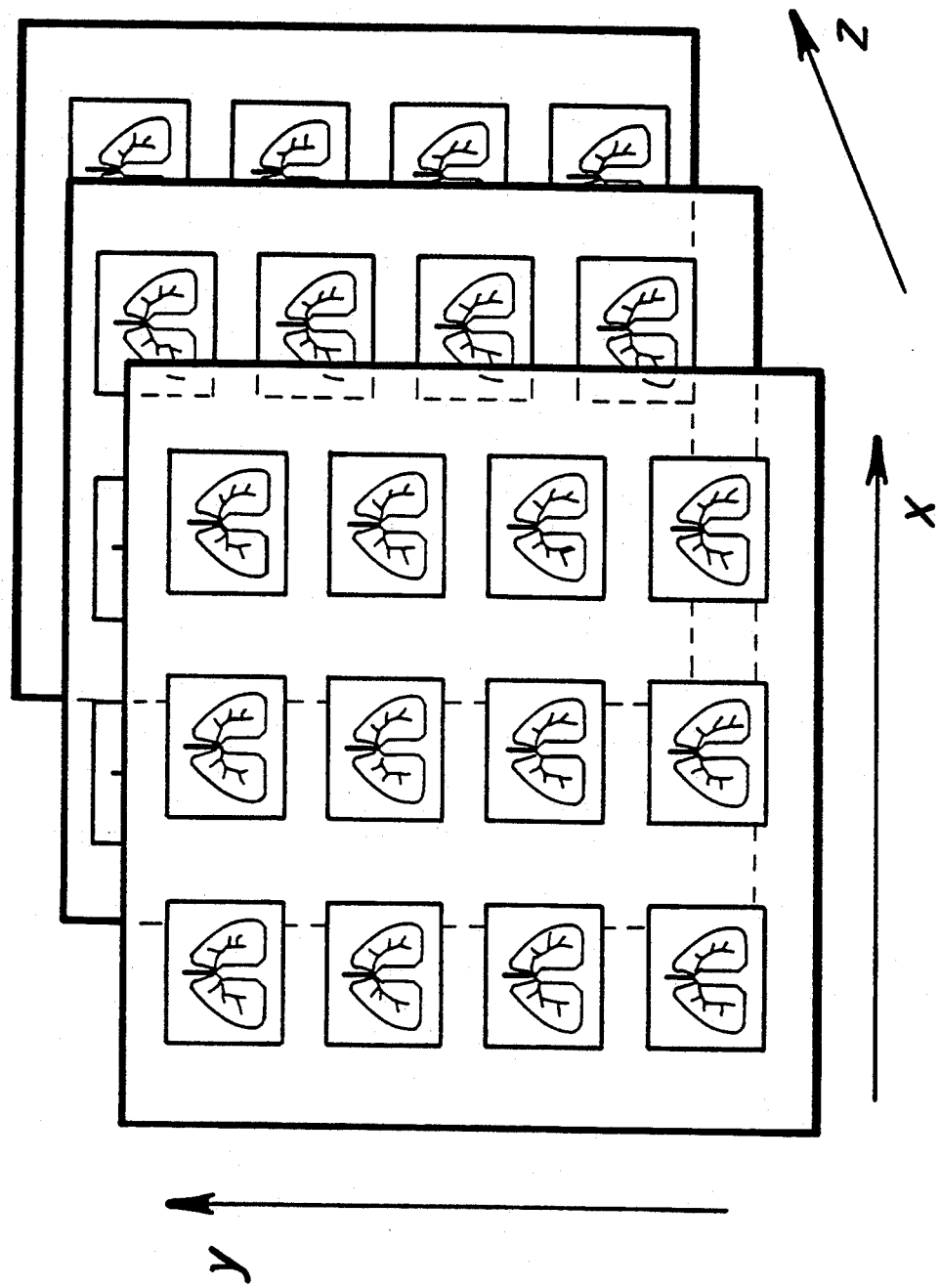
FIG. 8: THREE-DIMENSIONAL CEL MATRIX

APPARATUS AND VISUAL DISPLAY METHOD FOR TRAINING IN THE POWER USE OF AEROSOL PHARMACEUTICAL INHALERS

BACKGROUND OF THE INVENTION

1. Field of the Invention

The field of this invention relates to inhalation therapy devices and incentive spirometry. More particularly, the field of the present invention relates to an apparatus and display method for interactive training in the use of metered dose aerosol inhalers.

2. The Background Art

Devices for dispensing aerosol pharmaceuticals have become the favored medication delivery system in the treatment of many respiratory diseases. The use of inhaled sympathomimetic bronchodilators has been widespread since the 1960s. Moreover, the past several years have witnessed a rapid increase in the prescription of inhaled corticosteriods. In addition to these medications, whose primary site of action is in the respiratory tract and lungs, the inhaled route is being explored for the delivery of systemically acting pharmaceuticals.

Inhaled pharmaceuticals have taken a central role in the treatment of common diseases such as asthma, bronchitis, and emphysema, and their use is expected to increase. Approximately 10 to 15 million people in the United States suffer from asthma, and its prevalence in the general population is increasing. Childhood asthma is the single greatest cause of missed school days in the United States, accounting for an estimated 10 million absences in 1990. Chronic obstructive lung disease (COPD) of all types is estimated to affect as many as 30 million in the U.S. See Petty, "Chronic Obstructive Pulmonary Disease - Can We Do Better?," Chest, 97:2(S), (1990).

Inhaled aerosol treatment has been found to be extremely effective for respiratory disease, since medication is delivered directly to the site of action. In comparison with other routes of administration, this reduces the dosage required and in some instances speeds the onset of action. Inhalation of a pharmaceutical resembles parenteral injection because it bypasses the liver and thus reduces hepatic metabolic degradation of the active compound. See Reed, "Aerosol Glucocorticoid Treatment of Asthma," *American Review of Respiratory Disease*, 141:S82-S88, (1990).

it has been found that aerosol delivery of a pharmaceutical such as a glucocorticoid has significant advantages over oral administration in terms of reducing adverse side effects. For example, osteoporosis, compression fractures of the vertebrae, and aseptic necrosis of the femoral head are well known serious complications of prolonged oral glucocorticoid treatment. These side effects have not been reported in patients who have received glucocorticoids through aerosol therapy. Id. Similarly, adverse reactions caused by bronchodilators, including tremor and tachycardia, are reduced when delivery is switched from oral to inhaled routes.

Such benefits are due at least partially to the reduced dosage necessary to effect therapeutic benefit when these pharmaceuticals are administered through inhalation. When aerosol glucocorticoids are substituted for oral treatment, the dose of prednisone or prednisolone required to maintain control of airways can be more effective than an administration of 20-80 times the dose of the same drug by mouth. Id.

As treatment of diseases with aerosol pharmaceuticals such as aerosol glucocorticoids increases, there is a need for more efficient delivery systems to ensure proper delivery of the therapeutic agent into the lungs. Proper inhalation techniques are essential in order that the inhaled pharmaceutical such as a glucocorticoid is delivered to the receptor sites in the lungs. If the glucocorticoid aerosol lands in the pharynx or other part of the respiratory tract other than the lungs, its beneficial effect is lost or reduced. Moreover, the improperly delivered aerosol glucocorticoid can be digested by the system, resulting in the adverse side effects which aerosol therapy is intended to overcome.

A major problem in the use of aerosol pharmaceuticals is achieving deposition of the aerosol at the target receptor sites within the airways and lungs. Pressurized metered dose inhalers have been designed to deliver a precise amount of medicine in the form of a cloud of aerosol droplets having an aerodynamic diameter which is optimal for reaching the conducting airways of the lungs. Similarly, dry powder generators have been designed to deliver a measured amount of dry particles, such as sodium cromoglycate, to the lungs.

The human lung divides dichotomously for some 23 generations until the alveoli are reached. Inhaled aerosol medication particles must move through airways of ever decreasing size, at decreasing flow rates, while constantly changing direction. As a result primarily of impaction on the sides of the inhaler device, the mouth, and the oropharynx, only a small fraction of the dose from a aerosol inhaler is actually deposited in the lungs. This is true even when the inhaler is used according to the manufacturer's instructions. When the patient uses the inhaler incorrectly, the dosage delivered is greatly reduced. Newman, et al., "Deposition of Pressurized Aerosols in the Human Respiratory Tract," Thorax, 36: 52-55 (1981). Patterson et al., "Patient Error in Use of Bronchodilator Metered Aerosols," *British Medical Journal* 10:76 (1976).

So many patients use inhalers improperly that poor inhalation technique is believed to be the main reason for the lack of efficacy of aerosol bronchodilators and aerosol glucocorticoids. Because breathing habits are subliminal and developed over the course of a lifetime, it is especially difficult for a patient to alter inhalation techniques in order to increase the efficacy of an aerosol medication. Reed, "Aerosol Glucocorticoid Treatment of Asthma," *American Review of Respirator Disease*, 141:S82-S88 (1990). (cite Lancet editorial)

The literature is replete with examples which indicate the magnitude of this problem. In 1976, Orehek, et al. tested 20 asthmatic patients using bronchodilator drugs. Of these, only five used proper inhalation techniques. See Orehek, et al. "Patient Error in Use of Bronchodilator Metered Aerosols," *British Medical Journal*, 10:76 (1976). It was also reported in 1980 that 47% of 30 patients hospitalized for asthma used an incorrect inhalation technique. Shim and Williams, *The American Journal of Medicine* 69:891-894 (1980).

Although coaching can improve the ability to use inhalers, it has been found that many patients revert to an incorrect inhalation technique within a short period. Importantly, it has been concluded that regular subsequent monitoring of inhalation techniques are necessary. Patterson, et al., "Use of Pressurized Aerosols by Asthmatic Patients," *British Medical Journal*, 10:76-77 (1976). Because the full potential of aerosol pharmaceuticals cannot be achieved unless patients understand how to properly use inhaler devices, there is a need to more effectively train patients to follow a proper sequence of inhalation steps to be followed in order to ensure maximum delivery of an aerosol pharmaceutical to receptor sites in the lungs.

Methods of teaching proper inhalation may require complex breathing patterns. Aerosol pharmaceuticals are deposited in the lungs by three principal mechanisms: inertial impaction, gravitational sedimentation, and diffusion. Other mechanisms of deposition such as electrostatic interactions with opposite charges in airways walls are so small as to be insignificant relative to these three processes.

Impaction of aerosol particles or droplets on the sides of the oropharynx and airways increases with increasing particle size and/or flow rate of inspiration. Sedimentation is a critical factor in determining the amount of aerosol deposited in the alveolar bed and conducting airways. Sedimentation is time dependent process and the level of aerosol deposition is therefore a function of the duration of the breath holding pause following inhalation.

The mechanisms of deposition have been clarified by scintigraphic studies. Such experiments demonstrate that inhalation at higher flow rates increases deposition in the oropharynx and upper airways, while decreasing deposition in the lower airways. These studies also illustrate an increased deposition with longer breath holding because the amount of aerosol remaining airborne decreases exponentially with time. In one study, radiolabelled aerosols were inhaled at varied lung volumes and flow rates and radiographic images taken to detect the distribution of aerosols within the respiratory tract of patients with obstructive airways disease. This study showed that increasing the length of breath holding from 4 to 10 seconds effectively doubled the percentage of medication deposited in the lungs. Newman, et al., "Effects of Various Inhalation Modes on the Deposition of Radioactive Pressurized Aerosols," *European Journal of Respiration*," Dis. Suppl. 119, 63:7 (1982).

Conventional methods and apparatus for inhalation training lack adequate visual representation of these and other processes that govern the actual delivery of the aerosol to the receptor sites in the lungs. Accordingly, there is a need for an inhalation training apparatus which will provide the patent and physician with a real time, interactive representation of the inhalation process. Ideally, this would provide visual feedback representing the actual distribution of inhaled aerosol in the lungs and show with reasonable accuracy the amount of aerosol delivered to the receptor sites. Such feedback would convey a conceptual understanding of the proper inhalation process, and thereby increase the likelihood that the patient would retain the correct technique.

Several attempts have been made to improve the usage of inhalers. For example, some devices attach the inhaler to spacer tubes which extend the channel through which the aerosol flows. A typical example of this device is U.S. Pat. No. 4,809,692 issued Mar. 7, 1989. This device provides an extended channel for the flow of aerosol in the form of a mask which fits over the nose and mouth of a child. The device includes an inhalation valve in which a sound is generated upon inhalation and exhalation.

Other attempts to improve the use of inhalers include providing large non-pressurized chambers or reservoirs for holding the aerosol prior to inhalation. These devices lessen or obviate the requirement for coordinating actuation of the inhaler with inspiration. Some of these devices also feature auditory signals which provide the user with feedback when the inhalation flow exceeds a desired rate. Examples of such devices are Sacker et al., U.S. Pat. No. 4,484,577, issued Nov. 27, 1984, Zoltan et al., U.S. Pat. No. 4,926,852, issued May 22, 1990, Zoltan, U.S. Pat. No. 4,790,305, issued Dec. 13, 1988, Grimes, U.S. Pat. No. 4,210,155, issued Jul. 1, 1980 and Sperry, U.S. Pat. No. 4,852,561, issued Aug. 1, 1989. While these devices have been found effective, many patients do not utilize them because of the inconvenience caused by their bulk and the patient's self consciousness about the use of such devices in public.

The foregoing devices still, however, provide an inadequate means for training the patient in proper inhalation techniques. While auditory signals may provide some feedback for breath intake, there is no means for measuring a patient's performance with a standard or optimum technique for delivering medication to the receptor sites in the lungs. There is also no means for showing whether the aerosol is in fact being delivered properly to the lungs. In addition, these devices provide no means for active guidance for breath holding at the end of aerosol inspiration.

Still other conventional inhaler devices attempt to maximize the delivery of an aerosol pharmaceutical to the receptor sites in the lungs by employing improved actuating mechanisms. An example of such a device is Wasf, U.S. Pat. No. 4,664,107, issued May 12, 1987. Similarly, Johnson et al., U.S. Pat. No. 4,803,978, issued Feb. 14, 1989 provides an inhaler device wherein the release of medication is actuated by a pressure drop at the time of inhalation. These devices are more complex and expensive than the simple inhaler devices currently in general use. Accordingly, their use has not become widespread. Moreover, while these devices address the problem of coordinating inhaler actuation with the start of inspiration, they do not address the need for teaching proper inhalation flow rate, volume, and breath holding time in order to maximize the amount of medication delivered to the receptor sites.

Typical inspiratory training devices also include a number of incentive spirometers such as Sharpless et al., U.S. Pat. No. 4,391,283, issued Jul. 5, 1983, or Lester, U.S. Pat. No. 4,284,083, issued Aug. 18, 1981. Conventional incentive spirometers include mechanical means for allowing the user to see a visual indication of the rate of inspiration or expiration. The user can then compare this with a desired value. The object of these devices is the promotion of post-operative recovery of the lungs. To effect this they provide an incentive for the patient to expand the lungs. These devices are not designed for teaching techniques for inhalation of aerosol medication.

Therefore, such conventional devices have little or no usefulness in training a patient to use an inhaler device properly. For example, the incentive in the '283 patent resides in observing a cylinder or sphere raised to a predetermined height in a tube. This has the disadvantage of merely measuring flow rate or volume of inhalation. Thus, it ignores many of the parameters responsible for specific deposition patterns of an aerosol pharmaceutical at the receptor sites in the bronchial tree. Here again, the patient is not provided with any visual feedback relating to the delivery of an aerosol medication to the lungs.

Elson, U.S. Pat. No. 4,241,739, is a typical incentive spirometer device intended to promote post-operative recovery. This device incorporates a flow meter, processing means and display means to provide visual feedback of the volume of airflow during inhalation. However, this device is of limited usefulness in that it only takes into account a few limited parameters in defining the program of respiratory exercise which the patient is to follow. The parameters include minimum flow rate to be achieved, minimum total volume to be inhaled, the time that the patient is to hold the inhaled volume, and the number of times the patient is to be required to inhale the predetermined minimum volume. The feedback to the patient consists of display windows comprising an array of light emitting diodes which display alpha-numeric characters. For example, the flow rate of the air inhaled by a patient is integrated to determine volume. If the volume of inspired air by the patient exceeds that amount which was set by the therapist into a volume register, the display panel is instructed to display the word "Good." This device has the disadvantage of limited feedback to the patient. Also, the feedback is not interactive. The values of the desired parameters such as minimum flow rate, minimum total volume to be inhaled or number of inhalations must be predetermined by the therapist and then programmed into various memory registers. The patient's responses are then compared against the predetermined values. Accordingly, this device, in principle, is not too far removed from a conventional mechanical incentive spirometer having feedback such as the distance an object rises in a calibrated tube.

A typical inhalation training device also includes a "Respiratory Biofeedback and Performance Evaluation System" Hillsman, U.S. Pat. No. 3,991,304 1976. This system relates to performance evaluation and training in repetitive breathing patterns. The object of this system was to improve the efficiency of a patient's ongoing breathing pattern, in order to increase oxygen supply and carbon dioxide elimination to and from the lungs. The uses contemplated for the Hillsman system did not achieve commercial success or widespread application. These uses include repetitive breathing patterns characterized in terms of three inter-related factors: rate of respiration, tidal volume, and inspiratory to expiratory time ratio. The system provides a conventional visual display for patient training wherein volume of air inspired or expired is plotted on a vertical axis against time as represented by the horizontal axis, with cycle time or breathing rate adjustable from 0 to 40 cycles per minute.

The conventional Hillsman training system focuses primarily on the cyclic breathing of individuals with obstructive or restrictive lung diseases, with or without the concurrent inhalation of aerosols. Training is also contemplated for individuals engaged in intermittent positive pressure breathing, the playing of musical instruments, scuba diving, and Lamaze-type obstetrical breathing exercises. Techniques associated with cyclic breathing are different in nature from those involved in a discrete, individual inhalation and breath hold maneuver. A conventional inhalation training system does not address the particular problems associated with the use of a hand held metered dose inhaler. For example, maximizing the delivery of medication from a metered dose inhaler involves a discrete, one-time action of a single inspiration and breath hold maneuver wherein no relation exists with breathing cycles immediately prior to or subsequent to the studied inhalation itself.

Another example of a conventional inhalation trainer is a device marketed by Vitalograph Corporation of the United Kingdom and Lenexa, Kans. This device includes a metered dose inhaler connected with a flow sensor and means for calculating flow and volume of air. The display of feedback to the user is in the form of lights of alternating color and an analog needle gauge which indicates flow rate, including a desired flow range. During the practice inhalation maneuver, the patient is told to keep the needle gauge within the desired flow range. At the completion of the maneuver the device displays three colored lights, labeled "firing," "delivery," and "breath hold". A green light indicates that the patient performed the corresponding aspect of the inhalation correctly. A secondary optional display provides an incentive device utilizing several lights overlain with cartoon figures painted on a plastic overlay. At the conclusion of the maneuver the lights are illuminated under certain of the cartoon figures, indicating thereby whether the three aforementioned aspects of the maneuver were performed correctly.

This device has the disadvantage that the feedback provided by the colored lights is not fully interactive. In addition, the device does not provide feedback regarding the patient's performance across the full time course of the maneuver, since the flow gauge represents only an instantaneous indication of flow. In addition, the device does not allow the operator to change the values which differentiate between correct and incorrect performance. Furthermore, the device does not provide a printed or electronically stored record of performance.

The prior art also includes an MDI Biofeedback Training and Evaluation System, Hillsman Patent 4,984,158 1991. As in the system described in Hillsman 1976, this training system is based upon a volume versus time graph of patient breathing patterns. The system employs an MDI canister, flow measurement means, processor, and means for displaying actual breathing and desired breathing patterns. One of the integral elements of the Hillsman system is the measurement of both inspiration and expiration prior to, during, and after use of a MDI. Another element is the identification of the patient's lung volume at the point of start of inhalation.

Scintigraphic studies of aerosol deposition have shown that lung volume at start of inhalation is of secondary importance as a determinant of the level of aerosol deposition, in comparison with the factors of inhalation rate and duration of breath holding. For example, Newman, et. al reported that varying the start of inhalation point between 20%, 50% and 80% of lung capacity resulted in little difference in the percentage of aerosol deposited in the lunge, provided that proper inhalation rate and breath hold time were observed. Newman, Stephen P., et. al., "Effects of Various Inhalation Modes on the Deposition of Radioactive Pressurized Aerosols", European Journal Respiratory Disease Supp. 119, Vol 63, 1982. Thus, it appears that the careful measurement of end expiration point as a means of enforcing start of inhalation from low lung volume is of limited value. The inventors have in fact found that insisting that inhalation begin from low lung volume can actually impair the patient's ability to perform an optimal maneuver. This is because inhaling to full vital capacity at the desired low flow rate takes additional time, and increases the discomfort felt during a full ten second breath hold period.

The improvements offered by the present invention relate to both the manner in which airflow into the lung is measured and the structure and content of information displayed to operator, patient and physician. In the present invention the measurement of expiratory flow is eliminated altogether. This allows the patient to interact with the training system in a manner essentially equivalent to that which occurs in the normal use of a hand held inhaler. This is possible because whereas the canister holding component of a MDI is designed to allow sufficient airflow during inspiration, it does not provide a channel for unimpeded flow of expiratory air through the inhaler. To measure directional flow during aerosol usage, the Hillsman 1991 system attaches the MDI canister to an airflow channel through which the patient must breathe both in and out. In contrast, using the present invention the patient holds the MDI in hand during inhalation just as in everyday use, and removes the device from his mouth at the end of inhalation as in everyday use. This manner of MDI use is likely to be more effective in training since it more closely recreates the technique and situation of actual MDI use.

Another disadvantage of the Hillsman design is the requirement for the patient to direct his attention to the volume signal and hold the flow tube in his mouth throughout the breath hold stage. This procedure is counter to the normal practice during MDI usage wherein the patient removes the inhaler from his mouth at the completion of inhalation. Patients are in fact specifically instructed in the inhaler medication package insert not to breath out through the inhaler, since this may clog the MDI nozzle with exhaled medicine. In the Hillsman system the volume-time signal is also used as the primary feedback mechanism to the patient regarding the duration of breath holding. The message format utilized in the present invention, a timer, written message, and/or graphic portrayal of dynamic aerosol deposition via sedimentation and diffusion, is again more intuitively understood by the patient and is compatible with the normal circumstance and feel of MDI usage.

An advantage of the present invention is the use of patient feedback display types which are inherently more responsive and interactive than a volume-time graph. By employing a flow-time or flow-volume graph as feedback to the patient, subtle changes in inhalation rate are conveyed almost instantaneously. Moreover, since a primary object of the training is to teach the feeling associated with correct inhalation flow rate, the use of flow as a primary feedback signal is more intuitive to the patient.

In summary, the foregoing conventional inhalation training devices ignore or discount variables which are important in maximizing the amount of and rate at which the aerosol medication is delivered to the receptor sites in the lungs. Conventional devices also ignore the complexity of mechanisms responsible for the deposition patterns of an aerosol medication in the lungs.

Conventional devices do not offer the patient a visual form of feedback from which to conceptualize the process of medication delivery. Typical feedback mechanisms such as red and green lights, analog needle gauges, or alphanumeric characters indicating "good" are merely generalized, gross indications of the amount of air inspired. Effectively, such gross indicators are, in principle, unchanged from devices wherein the feedback consists of an object rising in a calibrated tube. Simple graphs of lung volume are similarly inadequate to convey the needed conceptual understanding.

Thus, there presently exists a need for a device which provides meaningful visual feedback to a patient in order to train the patient to use an aerosol inhaler effectively over the long term.

The typical inhaler devices and training aids have little or no diagnostic value and provide the physician with little or no meaningful objective feedback concerning the capability of a particular patient to effectively utilize aerosol therapy devices. There is also a need for an inhalation training device which can be used simultaneously by the patient and the medical professional and which can present to the medical professional a detailed illustration of the overall pattern of individual patient performance as opposed to a general indication of good or bad performance. There is also a need for visual feedback provided to a patient or healthcare professional that is directly related to and indicative of the complex physiological parameters which are different for each patient and which largely determine the pattern of distribution of the aerosol medication at the receptor sites in the lungs.

In order to improve the aerosol delivery of medication, what is needed is a device which takes into account a maximum number of meaningful parameters affecting aerosol distribution at the receptor sites in the lungs. These parameters include airflow rate, inhalation volume, duration of inhalation, duration of breath holding and patient-specific pulmonary function values such as vital capacity and timed flow rates, and disease conditions such as obstructive illnesses which lower the optimal inhalation rate. What is also needed is a method for interpreting the values of the variables affecting aerosol distribution and utilizing this interpretation to modulate the feedback display to the patient to produce meaningful interactive visual feedback representing the present state of delivery of medication to the target receptor sites in the patients' lungs.

Therefore, what is needed is an apparatus and visual display method which provides meaningful feedback to a patient and healthcare professional in order to train the patient to effectively use an aerosol inhaler over the long term. This system would recreate the normal feeling of hand held inhaler usage, and convey a conceptual understanding of the correct, although counterintuitive, inspiration and breath holding pattern. Such a system would teach the patient the specific skills required to affect delivery of medication to is target sites of action.

SUMMARY OF THE INVENTION

A first aspect of the invention provides an apparatus and display means for interactive training in the use of pressurized aerosol inhalers. The apparatus comprises an inhaler device containing a pressurized canister of medicine or placebo aerosol, a flow measurement device coupled with the inhaler device so as to measure the flow of air through the inhaler device, a microprocessor means for integrating the flow of air over time to produce a measure of the volume inhaled, a storage means for storing flow and volume values as well as other quantifiable parameters relating to patient lung function and projected patterns of aerosol deposition in the respiratory tract and an electronic visual display means for presenting flow, volume and time values as well as diagnostic parameters and/or illustrations of projected delivery of aerosol to receptor sites during the period of use of the inhaler device whereby the measured values may be contrasted with desired levels for those values.

The device further includes a means for recording start of inhalation, duration of inhalation and duration of breath holding. The display means is capable of a substantially real-time display (e.g., less than twenty millisecond delay). Optionally, the device may include a means for recording the time of inhaler device actuation for use in calculating the relative timing of device actuation.

The longer time a person inhales, the shorter the time he or she will be able to hold their breath. The time elapsed during inhalation is a function of the volume is inhaled prior to breath-holding. When inhaling unit doses of medication, there is little benefit from inhaling more than a given volume. Moreover, breath-holding at high lung volumes is more likely to bring on anxiety (particularly in an obstructed patient) than breath-holding at normal tidal volumes. Thus, for practical purposes, the sum of the inhalation time plus the breath holding time should not exceed a designated number of seconds. If that total time is 12 seconds, then the inhalation-training procedure would be set up to have the person inhale for 2 seconds followed by breath-holding for 10 seconds. Inhalation time is likely to be a minimum of 1.5 seconds and a maximum of 4 seconds and inhalation volume to be a minimum of 1.0 liters and a maximum of 4 liters. In addition, the procedure would include having inhalation begin within a given time (e.g., 0.5 seconds before to 0.2 seconds after) relative to medication release.

In one display format, real-time values of flow and volume are graphed on an X-Y axis, wherein the X axis may represent volume and Y axis, flow. A target envelope is overlain upon these axes to indicate a range of desired values within which the aerosol medication is effectively delivered. The display means includes means for superimposing the measured values of the patient simultaneously on the target envelope in order to provide visual feedback of the patient's inhalation. These values may then be compared with desired levels displayed in the target envelope.

Alternatively, the X and Y axes may represent flow and time, or both flow and volume versus time.

The target flow and volume values are based upon guidelines recommended by medical authorities. Alternatively, the target values may be based upon 1) predicted lung volume and timed flow rate values of a specific patient as calculated using regression equations in accordance with techniques which are well known in the art, or 2) measured values of a patient's actual lung volumes and timed flow rates.

An alternate display format takes the form of a two or three dimensional graphic portrayal of the human lungs and tracheo-bronchial tree within which is illustrated the flow of aerosol in response to simultaneous flow and volume measurements of a patient's breathing. In a preferred embodiment of the invention, both the graphic lung portrayal and X-Y type feedback are displayed simultaneously.

It will be appreciated that each of these formats provides the advantage of an interactive, enhanced feedback over conventional inhalation training devices. This greatly facilitates the learning of proper breathing techniques for maximizing delivery of aerosol medication from a metered dose inhaler to the receptor sites in the lungs.

In accordance with another aspect of this invention, the graphic display format also illustrates the deposition of an inhaled substance by impaction, sedimentation and diffusion in the mouth, oropharynx, airways or alveoli, and its expulsion out of the lungs during expiration. It will be appreciated that this display format presents the patient with a readily understood series of graphic images of the aerosol inhalation process. Such a series of images can provide the patient with an enhanced conceptual understanding of both the correct inhalation procedure and the linkage between the correct procedure and successful delivery of the aerosol medication. Such a visual and conceptual understanding may reduce the need for frequent re-training in inhaler usage.

It will be further noted that these display formats can provide the physician with a meaningful therapeutic tool which provides objective data on aerosol delivery. This data can aid in diagnostic activities and in the evaluation of patient response to pharmacologic therapies. This is increasingly important in the asthma area, as treatment protocols have shifted to a greater reliance upon anti-inflammatory medications such as corticosteroids. Since the effectiveness of corticosteroid therapy for a specific patient can only be determined after several weeks, it is extremely valuable to have an objective measurement of proper versus improper usage of the medication by the patient.

In accordance with another aspect of this invention, the graphic display format may be stylized or may be represented by software generated animations of cartoon characters, or circles, spheres, or other abstract shapes. The display format is not limited to any particular geometric representation. On the contrary, the values of the variables governing aerosol distribution in the lungs may be used to modulate a display of a matrix of any graphic images capable of conveying meaning and discrimination.

In accordance with another aspect of this invention, the graphic display depicting the lungs or abstract shapes may take the form of a three dimensional display based on techniques involving, but not limited to, holograms, rotating mirrors, stereoscopic glasses and other devices.

According to another aspect of the invention, the display format may consist of a combination of feedback types wherein both the target envelope format and graphical images are displayed simultaneously. In such cases, the display may utilize a subsection of the display area to contain the X-Y axes format and another section to contain the graphical representation format.

In accordance with yet another aspect of the invention, the values of the specific parameters being measured may also be used to modulate and to produce other modalities of feedback. In one such instance an audio signal is generated having a specific tone when the values are within the target envelope. Such an audio signal would be used to augment the visual displays described herein.

In another embodiment of this invention any of these visual display methods of inhalation training may be implemented on a home video game apparatus such as those manufactured by Nintendo, Seaga or other sources. In this embodiment the software algorithms and graphics might be stored on a removable game cartridge and the hand held inhaler device might be connected to the game apparatus by means of a conventional input port commonly used to support a joystick or other device.

BRIEF DESCRIPTION OF THE DRAWINGS

FIGS. 4a through 4e illustrate an example of X-Y feedback to the trainee.

FIG. 4a shows an example of X-Y feedback target envelope.

FIG. 4b displays an example of X-Y feedback showing inhaled output kept within target range during a training effort.

FIG. 4c shows an example of X-Y feedback showing inhaled output kept within range until the end of the inhalation effort.

FIG. 4d shows an example feedback display to trainee during a timed breath holding stage.

FIG. 4e shows an example of a feedback display of performance results to healthcare professional and trainee.

FIG. 7 is a block diagram of the presentation of lung-portrayal feedback to the trainee driven by cel selection.

FIG. 8 shows an example of a three-dimensional matrix of cel selections representating variations in the inhalation, breath-holding, and exhalation processes.

DETAILED DESCRIPTION

Overall Apparatus

Figure 1A:
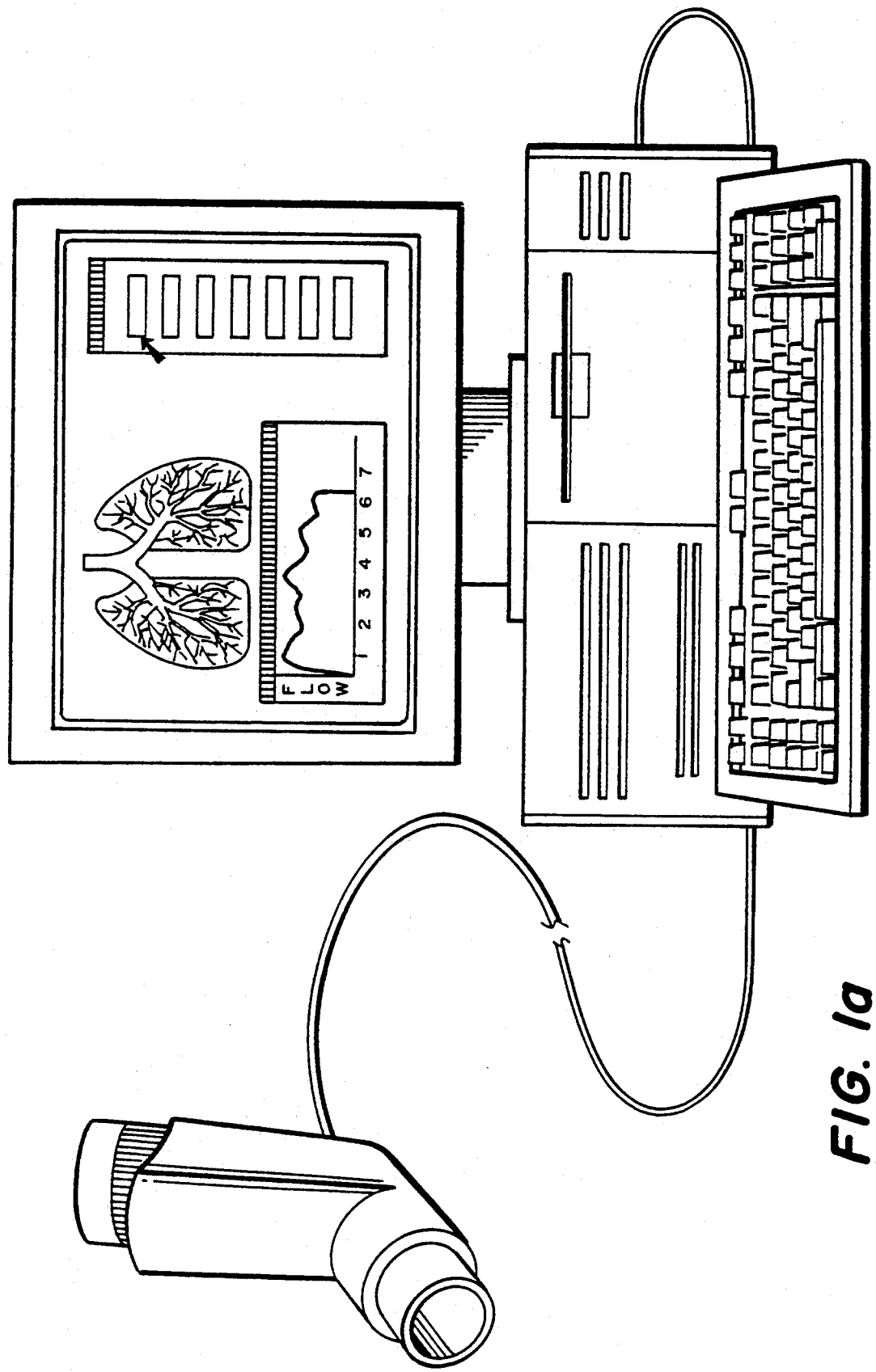
FIG. 1 is a plan view of the apparatus according to the present invention.
FIG. 1b is a block diagram of the overall system.
FIG. 1c is a block diagram illustrating an alternative arrangement of flow sensing elements.
Figure 1B:
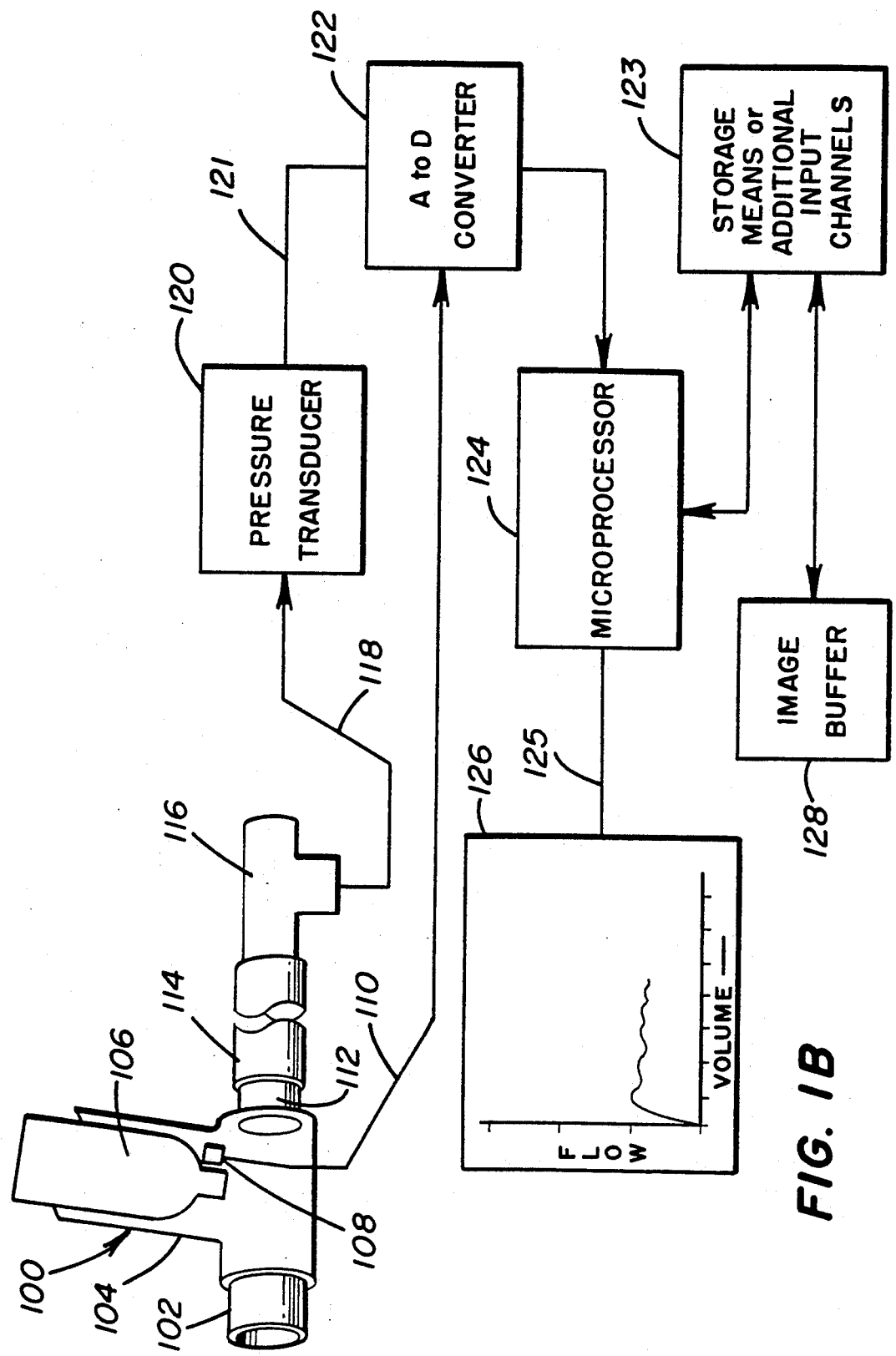

FIG. 1b shows a generalized block diagram of the inhaler training apparatus and display means according to the present invention. The apparatus includes a metered dose inhaler means 100 for dispensing a predetermined amount of aerosol medication into the mouth and lungs of a patient through mouthpiece 102. In a preferred embodiment, metered dose inhaler means 100 comprises a Ventolin (albuterol sulfate) inhaler such as that manufactured by Glaxo, Inc. The inhaler means 100 includes a dispenser housing 104 and a pressurized canister 106 for providing the propellant mechanism for discharging a metered dose of aerosol medication or placebo.

Optionally, the inhaler means 100 further comprises a sensor means 108 for providing an output signal on lead 110 every time the canister 106 is actuated. The inhaler means 100 is also attached through a coupler 112 and connecting tube 114 to a flow measurement means 114.

In a preferred embodiment, the flow measurement means 114 comprises a pneumotach or similar flow sensing device. The flow measurement means 114 provides a means for measuring the flow of air and aerosol through the mouthpiece 102 of the inhaler means 100.

The flow measurement means 116 provides calibrated pressure outputs which are conveyed through tube 118 to provide a measurement of the flow rate of the aerosol into a patient's lungs. The pressure outputs to tube 118 are input into a differential pressure transducer means 120. The differential pressure transducer means 120 provides an analog signal proportional to air flow output on line 121 to an analog to digital convertor circuit 122. The analog to digital converter 122 provides a digital representation of the flow rate to the microprocessor 124. The microprocessor 124 converts the voltage value to a flow value based upon conversion constants stored in memory 126.

A second input lead 110 of the analog to digital converter means 122 receives the output signal from the sensor means 108. This sensor detects the time of actuation of the aerosol canister 106 as represented by a sudden drop in pressure within the inhaler housing 104. The analog to digital converter means 122 provides a digital representation of the time of actuation to the microprocessor 124.

The A/D conversion would be typically 12-bit resolution since this is particularly appropriate to diagnostic spirometry as well, but this is not mandatory and lower or higher resolutions could be used. It should be noted that arrangement of the medicine container, flow sensing and A/D conversion elements described in this embodiment of the invention is particularly practical when the invention is incorporated within the context of a diagnostic spirometry system. When spirometry measurements are required, the use of smaller or less precise components is practical because the flow range relevant to inhaler training is narrower, and the required level of signal accuracy is lower.

Figure 1C:
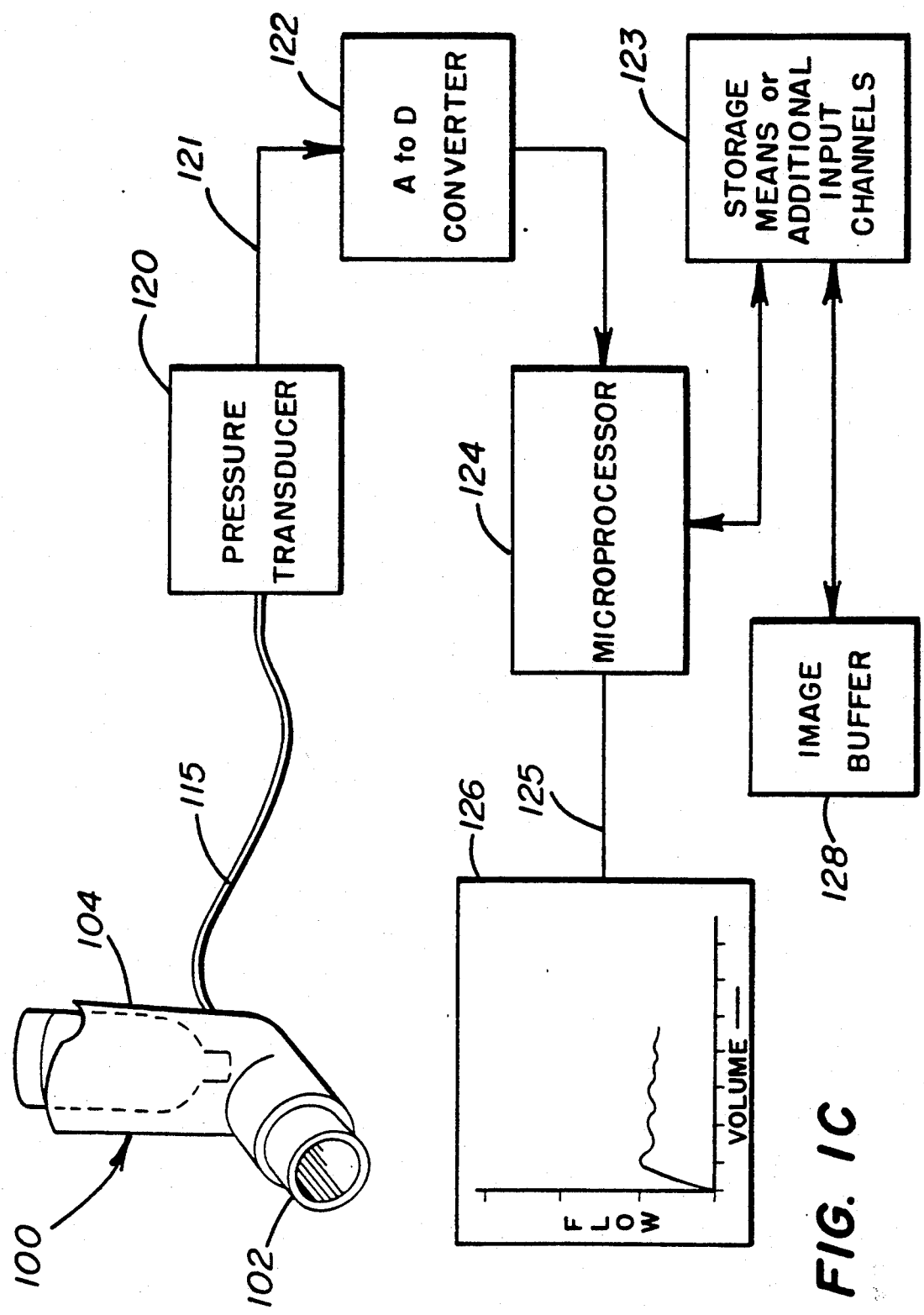
Figure 2A:
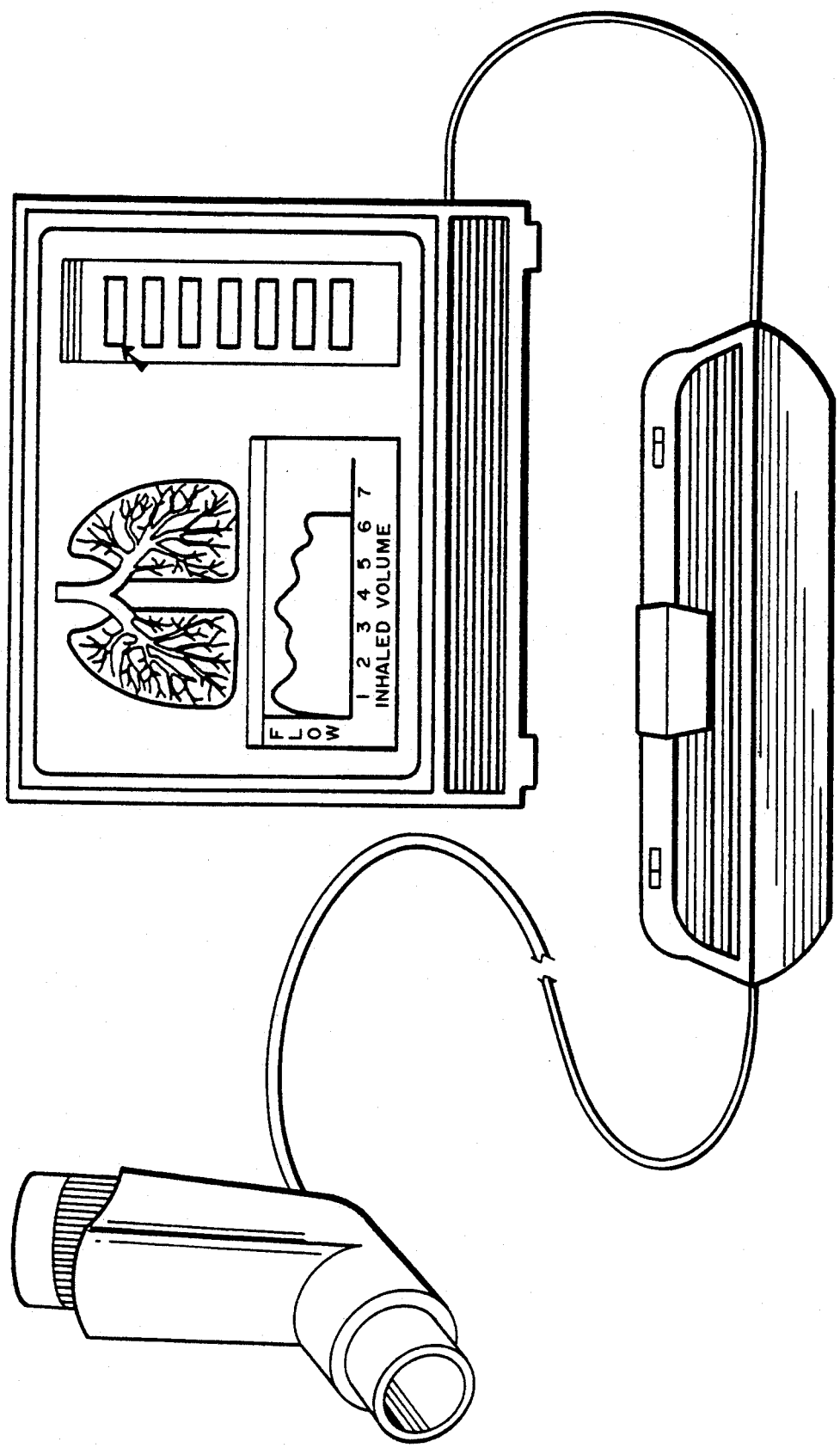
FIG. 2a is a plan view of the invention as implemented in the context of a video game apparatus.
Figure 2B:
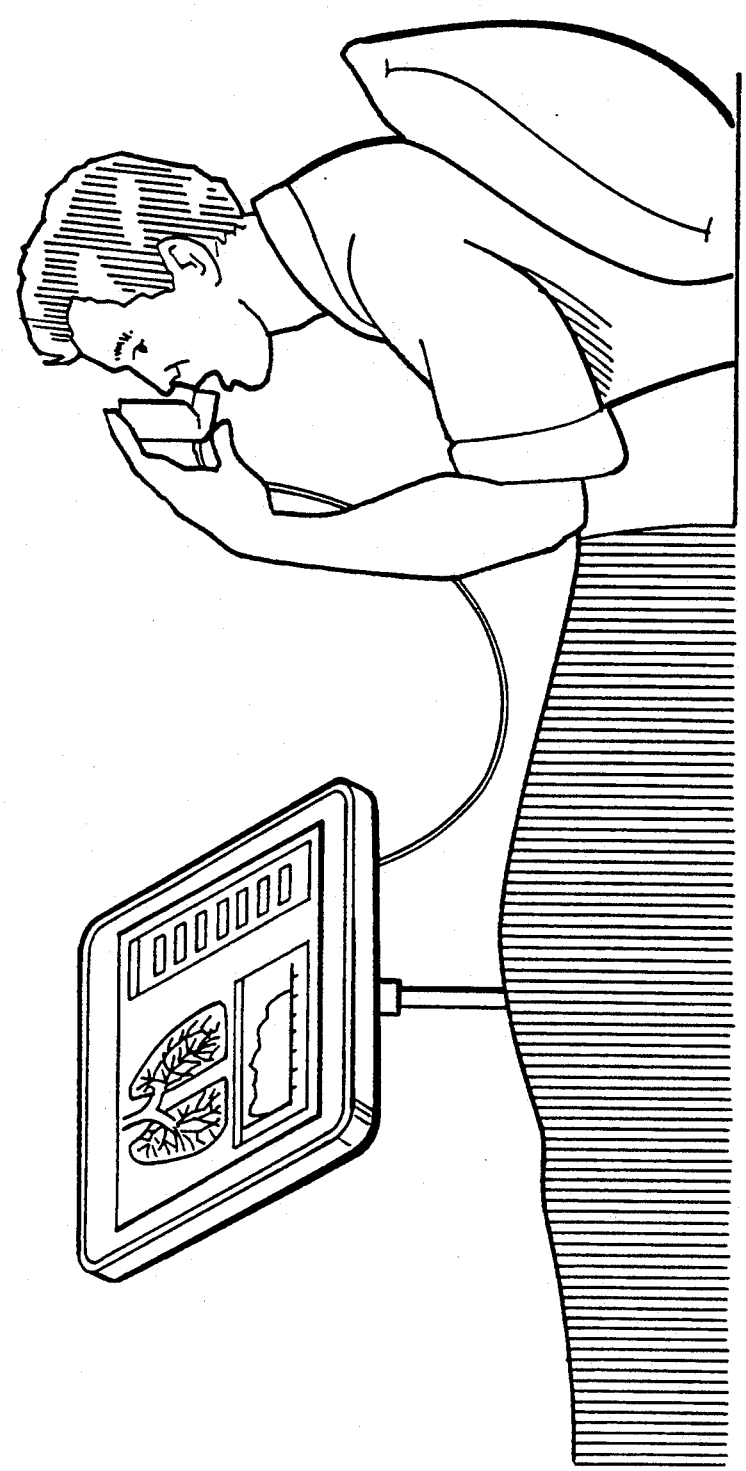
FIG. 2b is a plan view of the invention implemented in the context of a flat screen computer for use in a hospital setting.

In another particularly preferred embodiment (FIG. 1c), a simple pressure pickoff tube 115 is attached to the actuator housing. Pressure pickoff tube 115 is connected to a pressure-to-voltage transducer 120, e.g., Motorola MPX2010DP. The arrangement of elements in this embodiment of the invention (see FIG. 1a) allows the medicine actuator to be grasped in the hand by the patient as in everyday use (as shown in FIG. 2a). In this embodiment of the invention (referring again to FIG. 1c), inhalation through the actuator housing 104 causes a pressure drop to be conveyed via tube 115 to the pressure transducer 120. Transducer 120 is dual ported with the pressure sensed in the actuator housing 104 as compared to atmospheric pressure. Actuation of the canister 106 also results in a pressure spike which is detectable by transducer 120.

A further refinement would be the integration of flow sensing, digitization, and parallel-to-serial conversion elements within the hand held actuator housing, and the use of radio or infra-red communication to convey flow and other event signals to the microprocessor. This refinement has advantage of convenience associated with eliminating the tethered connection between the patient and the bulk of the training apparatus.

It should be noted that the microprocessor can also receive other input data via the analog to digital convertor 122 or other input channels such as from storage means 126. Such input data would represent additional events, values, or physiological variables which may have relevance to the performance of the inhalation.

The microprocessor 124 has an output lead 125 connected to a display means 130.

The microprocessor 124 includes a storage means 126. The storage means 123 includes an image buffer 128. The image buffer 128 includes a collection of electronically stored graphic images which can be displayed through the display means 130.

A permanent record of the test maneuver also may be provided by a printout or electronically stored data record for use by the medical professional and patient. The printout may include graphs of flow curves, calculated values and derived performance scores, as well as comments regarding the patient's performance and particular areas of difficulty. These comments may be input by an operator, taken from standard comment lists, or derived from calculations made upon test data.

Context in Which the Software Invention Executes

This invention is executable on any personal computer, workstation, or microprocessor-driven device. An example is the IBM AT or compatible computer using an Intel-compatible 80286, 80386, 80486, or succeeding generation microprocessor and running the DOS operating system and the Windows 3.0 or succeeding generation Graphic User Interface (GUI) environment. The invention could be run on IBM or compatible hardware running the UNIX or other operating systems or an Apple-Macintosh or compatible system, other personal computers, or on a workstation running the UNIX or other operating system. The invention could also be run on a video game apparatus or on a multimedia computer system or handheld personal computing device.

Referring again to FIG. 1A, the microprocessor hardware includes a Central Processing Unit (CPU), graphic display circuitry, Random Access Memory (RAM) main memory, Input/Output (I/O), resources to floppy and hard-disk drives, a keyboard, mouse (and-/or other pointing device).

As to programming language, the system implementation is projected at using C++, C, and assembly languages using object-oriented programming techniques, but other programming languages and programming methodologies could alternatively be used, including C without the use of C++.

Structure of the Invention

Figure 3:
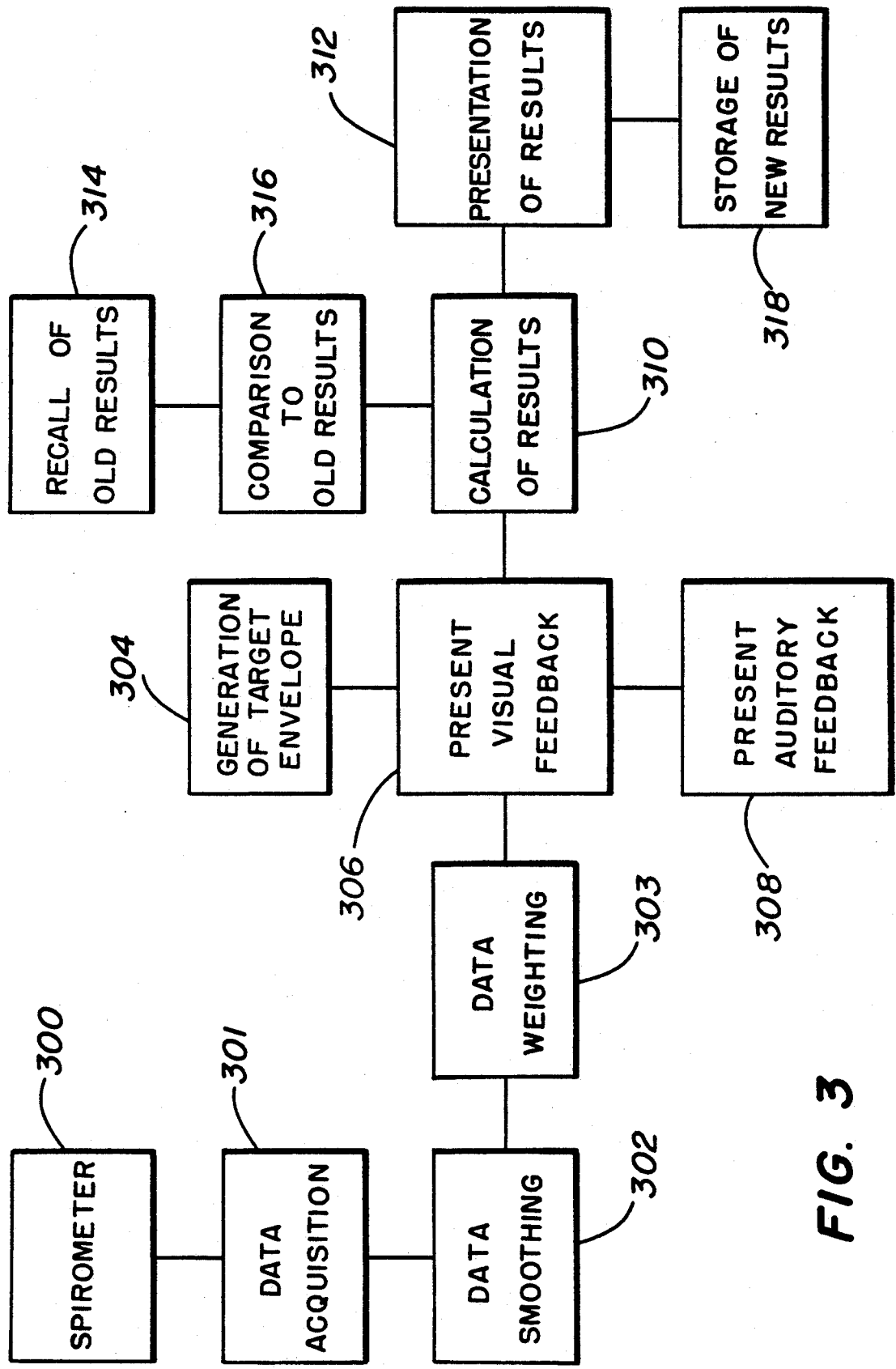
FIG. 3 is a block diagram of the overall process for the software component of the invention.

The major process components are shown in the block diagram in FIG. 3. The overall process involves: (a) Acquiring input data block 301 from the trainee as the patient inhales through the training device spirometer 300, (b) Smoothing the input data at block 302, (c) Optionally weighing the (smoothed) input at block 303, (d) Generating the target envelope 304, (e) Providing visual feedback to the trainee during the training maneuver on his or her performance relative to a target envelope at block 306. (This may be integrated with auditory feedback at block 308.), (f) Calculating an overall score on the exercise at block 310; (g) Presenting the final results to the patient at 312 (including optional recall 314 and comparison 316 to previous exercises on that or previous days); and (h) Storing those results 318. While the examples are in the context of pulmonary function, any medical variable under the control of a patient/trainee can be handled in an equivalent manner. A more detailed explanation of the foregoing process is provided as follows.

Acquisition of the Input Signal

Referring to FIG. 3, the spirometer block 300 includes the following elements; a pneumotach and a pressure transducer means for generating an electrical signal proportional to the pressure. The electrical signal is transformed in the analog-to-digital converter for further processing. The software includes the capability of calibrating the instrument in accordance with well known techniques.

Smoothing the Input from the Trainee

A smoothing function is useful to minimize noise in the signal (e.g., noise due to electromagnetic interference or vibration). Thus, the data may be optionally smoothed or filtered in accordance with well-known techniques.

Generating the Target Envelope

In each case, the trainee is trying to maintain the feedback representing his or her performance within a target envelope. The envelope will vary according to the type of feedback presentation. For example, in the case of x-y feedback, the trainee is attempting to maintain the line under his or her control within two horizontal lines representing the lower and upper bounds of desired flow (with volume or time as the x axis). Thus the target envelope to be generated is these two lines with the values set to default levels or set with reference to the individual trainee's physiological condition and the aerodynamics of what flow rate will optimize the delivery of aerosolized medication to the appropriate airway receptor sites.

Providing the Feedback to the Trainee

Two examples of feedback to the patient during inhaler training are the (a) x-y graphics as shown in FIG. 4, and the two-dimensional graphic lung portrayals as shown in FIG. 6. The output from the data collection passing through the microprocessor is the same, only its transformation in another step to a form that is suitable to the given display is different.

X-Y Feedback to Patient

The x-y versions of feedback include the target envelope that is related on the monitor screen to the actual inhalation effort by the individual being trained. In this case, the target envelope range is fixed, or is set through an algorithm relating the trainee's physiological condition projected at the time of inhaler training to the prescription of the optimal rate of inhalation maneuver required to obtain optimal benefit from the treatment. The target envelope range for any of the types of feedback can be related to the predicted pulmonary function capabilities of the trainee and/or selected by the operator.

Lung-Portrayal Feedback to Patient

Lung portrayals are of two types: (a) full views of the lungs and/or upper respiratory tract, and (b) views of a typical large or small airway. In each case, there is incorporated within the system a model of the flow of air and aerosol into and out of the lungs (and optimally expansion and contraction of the lung outline). The variables input are patient demographics and/or the physiological status of the patient's airways, and the data generated by the patient's inhalation effort. From these are calculated and displayed the intake and distribution of the air and aerosolized medication, and (optionally) the changes in the structure of the airways. The presentation of the lung-portrayal feedback can be the result of at least two processes: (1) an actual calculation based on a mathematical model of the involved pulmonary physiology, or (2) a selection from among candidate cels that have been previously prepared.

In the latter instance, the image cels are originally created using various technologies including bitmapped and vector-based graphics design tools. Once created and stored within the training system, individual static image cels are selected for feedback display according to the calculation of cumulative volume inhaled, flow rate over course of inhalation, duration of breath holding, and other factors. In this cel selection process the individual cel images themselves do not change.

In contrast, when feedback is derived from a mathematical vector model of the lungs, the current shape of the lungs and/or distribution of air and aerosol throughout the respiratory tract are continuously variable, and the image portrayed at any given moment is calculated in real time.

Because the lung portrayals are for educational purposes as opposed to being used for scientific research, it is not necessary that the model reflect exactly the anatomical structures or physiological processes involved. In regard to this point it is significant to note that several mechanical and mathematical models have been constructed to represent airflow within the human lung as a basis for calculations and predictions regarding the deposition of aerosols. Due to the complex morphology and dynamic structure of the lungs none of these models is considered to be highly accurate. However, an idealized model of aerosol distribution within the lung could incorporate equations which describe the processes involved in aerosol deposition to a degree of accuracy sufficient for patient training.

Portrayal of the lung in a three dimensional graphic format is preferable, and should provide the advantage of an enhanced training response. The instantaneous feedback in three dimensional form is now possible with conventional semiconductor logic and memory devices. As the cost of such electronic devices declines, they will be incorporated in low cost personal computer and video display systems.

Stylized (Cartoon) Feedback to the Trainee

Feedback to the trainee may also include modulating data values to portray visually any meaningful pattern of graphic images to present a target envelope for the patient and a means for discriminating an achieved result. For example, such graphic images may include the presentation of stylized cartoon feedback to the trainee. Like the lung portrayal, stylized feedback can be provided either based on a mathematical model or through cel selection.

Auditory Feedback to the Trainee

Auditory feedback to the patient can be similarly modulated. Tones increasing in intensity and/or volume are equivalent to the visually displayed x-y coordinates with the borders of the envelope provided by tones as well. Verbal feedback to the patient such as "faster, faster, ok, ok, ok, steady, steady, steady, etc." can be generated, and such feedback is roughly equivalent to the two- or three-dimensional graphic portrayals. The auditory feedback can be combined with visual feedback in a hybrid approach.

Calculating an Overall Score on the Exercise

In addition to the trainee and the trainer receiving interactive feedback on actual performance versus target, it is helpful to calculate an overall score or set of scores which represent the degree to which the inhaled medication is believed to have reached the target sites of action. Several functions predicting deposition by means of impaction, sedimentation and other factors could be translated into a single overall score indicative of patient performance. Such a score could be simplified to a rating on a scale of one to ten.

The amount of medication available to the lower airways and alveoli is equal to the amount released from the actuator less inertial-impaction losses. Of this amount, the quantity actually deposited at the target sites is a function of gravitational sedimentation and diffusion. Other factors such as electrostatic interactions with opposite charges in the airway walls and inertial impaction during exhalation are small and can be ignored.

While these variables cannot be directly measured in a given patient, they can be inferred. Inertial impaction occurs primarily in the mouth, trachea, and large airways and is proportional to inhalation flow rate. For the medication to be effectively delivered, the inhalation flow must be in a designated range (e.g., above 0.2 and below 1.0 liters per second). Gravitational sedimentation and diffusion occur mainly in the smaller airways and related in a sigmoid-curve function to the length of time the patient holds his or her breath. The amount of aerosol available (input) to the gravitational sedimentation and diffusion processes depends on how much is left after (the output) of the inertial-impaction process.

A preferred embodiment of a scoring mechanism which employs these observations is described as follows:

$$\text{The Deposition Score } (S) = F \times M \times D$$

Where
  $F$ = Scaling Factor
  $M$ = Fraction of medication reaching the lower airways, and
  $D$ = Fraction of medication M which is deposited during the breath holding process
Further,
  $F = 10$, since we want the score to be in the range from 0 to 10 (similarly, we would set $F = 100$ to have the score in the range of 0 to 100), $$M = T \times P$$

where
  T = (Total medication per actuation or "puff" of inhaler)
    which for scoring purposes can be set to 1 representing the best any patient could achieve
  P = (Percentage of inhaled volume in targeted flow range)
    which is measured, and
  D = a variable related to the measured time breath is held (usually set to 0.1 times the breath holding time B, so that $D = 1$ with an optimal breath-holding time of ten seconds).
where
  B = Breath holding time in seconds
  D can be refined to recognize the sigmoidal-curve nature of sedimentation over time. A sample equation is $$D = 0.1 \times (1 - \text{EXPONENT}(-10 \times (B/(10 \times (10 - B + 1))))).$$

In calculation of factor D, only breath-holding time in a selected range (e.g., 0 to 10 seconds) is counted since breath holding for longer than a given time (e.g., 10 seconds) does not significantly increase deposition.

Presenting the Final Results to the Trainee

One or more quantitative values are displayed to the trainee and the trainer. The display may optionally include a comparison to previous exercises on that or previous days so that progress (or regression) can be followed. For some, the idea of "high scores" and/or a "personal best" may have significant value as an incentive.

Storing Results

For future comparative purposes, the results of the training exercise can be stored on a hard disk, floppy disk, or other appropriate medium. If desired, the actual-performance curves can be stored in addition to the numerical or qualitative results.

Data Structures

The data can be represented in either integer or floating-point numbers as well as state or other variables or parameters that may be either text or numbers. The process does not depend specifically on the size of the bytes (usually 8-bit) or the particular internal scheme for representing floating-point numbers or integers. The data structure itself usually will be a mathematical array with indexed access with the index generated based on time or related variable.

Data Objects

One recommended embodiment is to use an object-oriented approach in which objects have both their data and the related behaviors incorporated within them. An example is a window object that knows how to display itself when a message to do so is passed to it. Child objects can inherit characteristics from parent objects and have selected attributes either modified by overriding the inheritance or added. Thus a visual feedback object might inherit the general characteristics of a parent visual-feedback class but within that child object specify its own particular behavior.

Note that while the process as described takes an object-oriented approach, there is nothing in this invention that would preclude an implementation using traditional programming approaches.

Description and Illustration of the Process Components

Stages of Maneuvers

There are three stages of respiratory maneuvers involved in inhaling a medication:

Stage 1: Inhaling the aerosolized drug,
Stage 2: Holding one's breath to allow deposition of the drug on lung-component surfaces, and
Stage 3: Exhalation.

If the trainee is cooperative, stage one will involve a monotonically increasing volume of the lungs, unless there is an interrupting event such as a cough that might be followed by a short inspiration. The main phenomena during stage two is sedimentation due to the force of gravity on the aerosolized medication droplets.

When the visual feedback to the patient includes a portrayal of the lungs, an outline of the lungs may be static throughout the three stages. If sufficient computer graphics processing power is available, the lung outline may expand and contract in response to the patient breathing. In this case during Stage 1 the envelope outlines will be increasing in size, in Stage 2, they will be (relatively) static, and in Stage 3 they will be decreasing.

The most important element of visual feedback when the lungs are portrayed is the distribution of representative droplets of aerosol medication. In Stage 1 they will move out to the periphery of the lungs as they go through the air passages with some deposition in the mouth, throat, and trachea, and on airway and on alveolar walls due to impaction. In Stage 2 maximum deposition on air passage and alveolar walls via sedimentation and diffusion will occur.

Driving the Feedback Process(es) by Trainee Input

The feedback is driven by the air flow input from the patient as the pneumotach transduced output is converted from analog to digital form and transformed to flow-versus-volume or flow-versus-time data.

Treatment of the Trainee Input

Two categories of treatment of the flow-versus-volume or flow-versus-time data are (a) smoothing of the input data, and (b) weighing of those data. In the former case, application of a smoothing function or filter can prevent the feedback from being unduly influenced by perturbations in the input signal (e.g., vibration or electromagnetic interference). In the latter case the signal may be modified to provide incentive.

Incentive Feedback

The purpose of the feedback is not just to give the trainee patient an indication of performance, but to ingrain trainee behavior that will optimize the deposition of aerosolized medication at the target sites. The goal of inhaler training is to cause the proper inhalation pattern for the medication to be made a habit. Sometimes, it may be easier to obtain the desired behavior if an incentive approach is used. This can involve a weighing function whereby the feedback to the patient is "accelerated" for values of input that are close to or above the Upper-target-envelope boundary.

Target Envelopes

The target envelope for inhalation is shown in FIGS. 1a, 2a, 2b and 4a-e. the context of flow-versus-volume axes. It also could be displayed in reference to a flow versus time curve.

The target envelope or "prescriptive target" for inhalation of the aerosol is determined by algorithms based on the race, height, and/or weight of the patient modified, if appropriate, by their condition. For example, if bronchospasm is present, more drug will be delivered if the flow rate is lower, thereby cutting down turbulence induced within the airways.

In the case of the x-y feedback, the target envelope for the y-axis measured variable (e.g., flow) is presented as two straight or curvilinear lines representing the upper and lower performance bounds allowing for optimal delivery of the aerosol to the lungs. A vertical line may also displayed to discourage inhalation beyond a predetermined volume. The x axis can represent either volume or flow. An example of such target bounds is shown in FIG. 4a.

Process Steps for Feedback to the Trainee X-Y Feedback

In the case of x-y coordinates, the target envelope 410 is "statically" displayed on the computer-monitor screen as was shown in FIG. 4a. Data are then collected during the inhalation-training effort, transformed to the appropriate variable, and displayed on the screen. The point of shift between the three stages can either be presented in a fixed manner or can be altered depending on the shift from the previous stage. For example, if the x axis represents time, once inhalation is completed the target envelope for breath holding can be "reset" to begin at the point inhalation actually left off, thus automatically resetting the onset time for the Stage-3 exhalation.

Figure 4E:
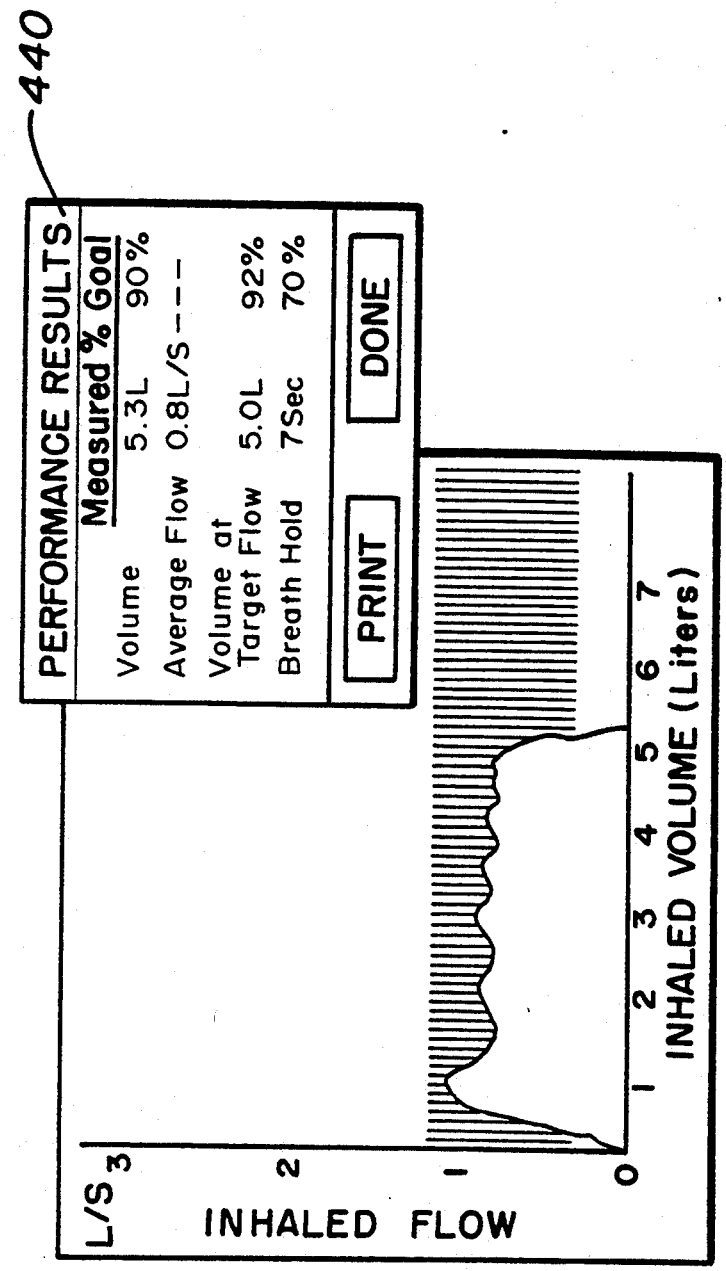
Figure 5A:
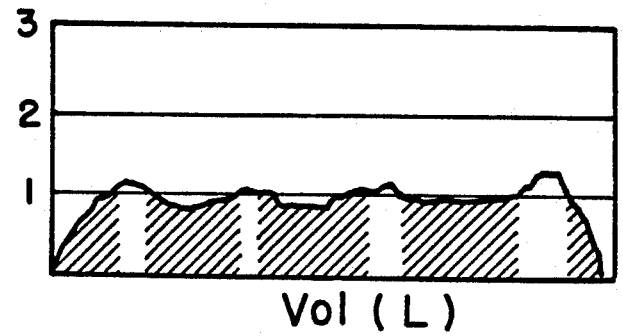
FIG. 5 is a sample method used to calculate an objective score rating the trainee's performance.
Figure 5B:
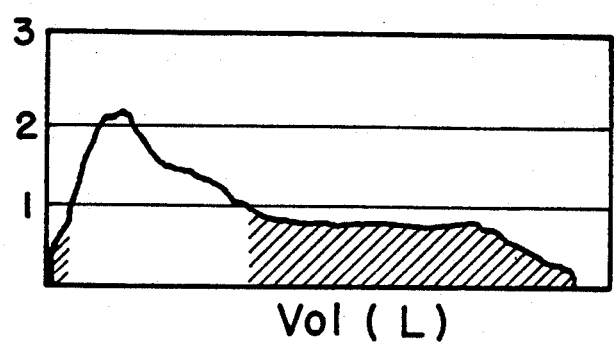
Figure 5C:
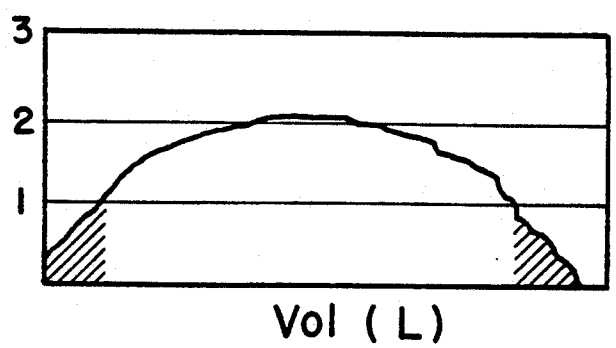
Figure 5C:
Figure 5C:
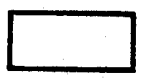
Figure 6A:
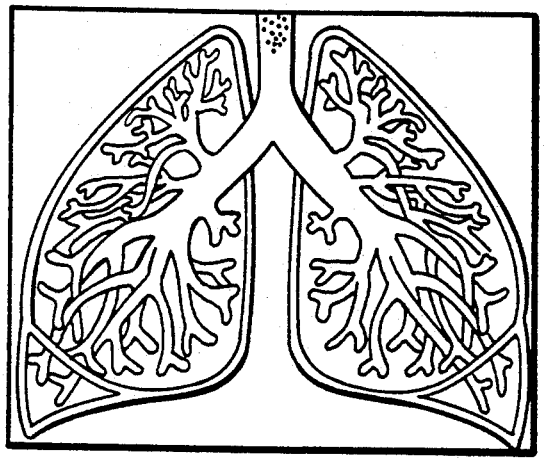
FIG. 6 is an example of a two-dimensional lung-portrayal feedback.
Figure 6B:
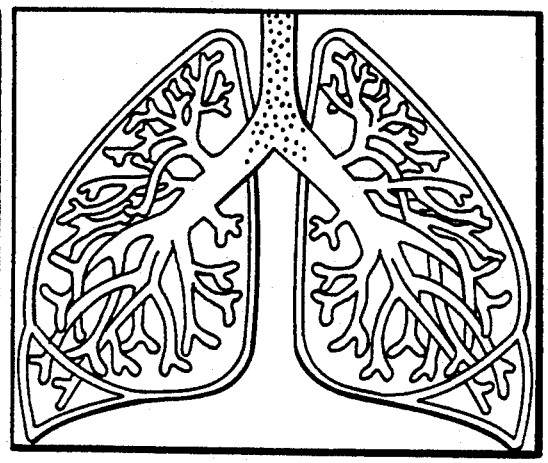
Figure 6C:
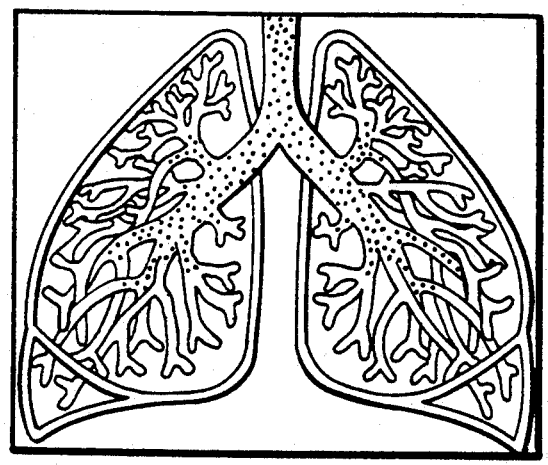
Figure 6D:
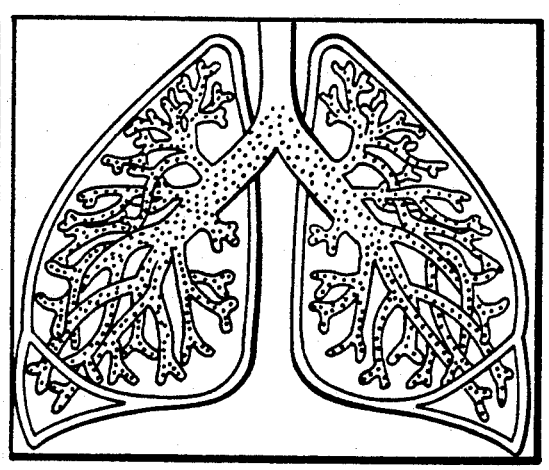

Stepping through one potential set of presentations, FIG. 4b shows an example of x-y feedback showing inhaled input 420 kept within range 410 during a training effort. In the next step, (FIG. 4c) shows an example of x-y feedback showing inhaled output 420 kept within range 410 to the end of the inhalation effort, just to the point of initiation of breath holding. FIG. 4d then shows an example feedback display to trainee during the breath holding stage during which a clock 430 is displayed to the trainee. A target clock time also could be displayed. Finally, FIG. 4e shows an example of a feedback display to trainee at the end of the inhaler-training effort showing the performance results 440.

Lung-Portrayal and Other Feedback to the Trainee

In the case of the two- or three-dimensional lung and/or component-airway portrayals, an image of the full respiratory tract, or of a subsection of the lower respiratory tract is displayed as a backdrop for illustrating the projected distribution and deposition of the aerosol medication. These pictorial representations can be generated in at least two ways. One method is to select (as a function of the independent variable - e.g., time or volume) the closest one of a multiplicity of candidate "cels". The second method is to generate a representation which approximates the patient's instant condition as a function of the independent variable(s) based on a two- or three-dimensional animated model. In the latter case, the position or state of the respiratory tract is calculated and displayed based on the model. In the former case, the individual candidate cels are fixed representations. These cels are previously generated from a model or prepared by an artist (e.g., through scanned renderings or use of a "paint" program). The representation may include a range of elements such as respiratory tract outlines, aerosol droplets of changing size and distribution, and backgrounds of airways and lung tissue with varied colors and shading.

A key aspect of all graphic portrayals is that the pattern of inhalation during stage one will determine the quantity of aerosol medicine reaching the lungs and thus the number (and size distribution) of droplets available for deposition by means of sedimentation and diffusion during the breath-holding stage.

The process for displaying the condition (of the patient's respiratory tract and medication within the airways) at a given point in time is similar whether the lung portrayal (or airway-cross-section stylized/cartoon representation) is done by model calculations or selection. The specific image displayed will depend on the preceding events which have been measured up to this point in the maneuver as modified by the current instantaneous value of the trainee's input function (perhaps as filtered and/or weighted). In the case where cels are used, each candidate cel in a category will have a single composite value. The candidate cel that has the closest value to that of the patient's current condition will be selected for display.

FIG. 7 shows a two-dimensional view of a graphic cel matrix. This matrix is of the same form whether the visual feedback consists of lung portrayals or stylized cartoons. FIG. 8 presents a sample three-dimensional "graphic matrix" presenting selectable cel representations for multiple combinations of events during the inhalation and breath holding stages.

Predicted Deposition Score

FIG. 5 shows a key element of the mechanism for calculating a performance score as described earlier. This is the calculation of the volume inhaled within the correct flow range, which is the chief factor determining the amount of medication which reaches the lower airways and alveoli. The figure illustrates the integration of volume inhaled while flow rate remained within the target envelope. More refined versions are possible (e.g., considering the degree by which a trainee was outside the target envelope). In Case A, there are only two relatively short periods during which the patient's inhalation flow rate falls outside the target envelope, representing ten percent of the total volume inhaled. In Case B, the flow is initially too high and remains so for 40% of the volume expired. In Case C, a broad middle section of volume inspired (80%) is outside the target envelope. This pattern is frequently observed in patients whose inhaler usage pattern is recorded while no feedback is being provided.

This same scoring mechanism can be used in conjunction with all types of feedback displays. At the time the final score is presented comparison to past performance in one or more previous exercises can optionally be displayed as well.

Besides the patient being able to determine visually whether the actual performance is correct, additional auditory feedback in the form of tone or computer-generated speech or visual feedback in the form of displayed text, changes in color, etc. can be supplied.

Pseudocode Description of the Invention

What follows is psuedocode for each of the major software functions as shown in the flow chart in FIG. 3. The pseudocode is the same for all feedback types. Details differ for those segments involving the feedback itself (including generation of target envelopes) and the calculation of results. These are covered by (a) presenting the common sections including generic pseudocode for the feedback presentation and results calculation followed by (b) more detailed pseudocode where the sections differ.

Data Acquisition 301
   SETUP analog-to-digital converter conditions;
   ZERO input from sensor;
   ACQUIRE input data on trigger;
   (Optionally) DETECT time of actuation Data Smoothing (Optional) 302
   ACCESS smoothing criteria;
   FILTER input data;

Data Weighing 303
   ACCESS weighing function;
   APPLY weighing to input data;

-continued

Generation of Target Envelope 304
  ACCESS target envelope according to selected visual and auditory feedback type;
Presentation of Feedback 306
  Begin:
    DISPLAY (next) target-envelope (if changed);
    DISPLAY trainee-generated visual feedback;
    (Optionally) OUTPUT trainee-result generated auditory feedback 308;
    IF finished with cycle THEN PROCEED,
    ELSE Begin;
Presentation of Breath-Hold Timing 306
  DISPLAY Hold Breath Timer;
  Cycle:
    INCREMENT time value;
    DISPLAY new value in Hold Breath Timer display;
    IF breath holding completed THEN Presentation of Results ELSE Cycle;
Calculation of Results 310
  CALCULATE difference between target envelope and trainee performance;
  CALCULATE quantitative estimate score of medicine deposition
  (Optionally) RECALL old results;
  CALCULATE COMPARISON to new results;
Presentation of Results 312
  DISPLAY results;
  (Optionally) DISPLAY old results 314;
  DISPLAY comparison to new results 316;
Storage of New Results 318
  ACCESS storage access information;
  STORE results;
  UPDATE indices to trainee data;
  The following modules are feedback specific and detail the above generic versions. They are presented in Target Envelope/-Feedback Presentation pairs.
Generation of Target Envelope for X-Y Feedback
  ACCESS constant lower straight-line displayed bound for flow versus volume or time according to prescribed training objective;
  ACCESS constant upper straight-line displayed bound for flow versus volume or time according to prescribed training;
  ACCESS constant lower-frequency bound (or other auditory variable such as word/phrase) for flow versus volume of time according to prescribed training;
  ACCESS constant upper-frequency bound (or other auditory variable such as word/phrase) for flow versus volume of time according to prescribed training;
Presentation of Feedback for X-Y Feedback
  DISPLAY lower bound of target envelope;
  DISPLAY upper bound of target envelope;
  (Optionally) COLOR between the boundaries;
Label 1:
  MEMORY-STORE trainee-generated value;
  DISPLAY trainee-generated visual feedback curve;
  (Optionally) COLOR area under feedback curve;
  (Optionally) IF trainee feedback outside the target envelope THEN COLOR region between feedback curve and boundary exceeded AND
  (Optionally) OUTPUT tone or word/phrase auditory feedback;
  IF finished with inhalation THEN Presentation of Breath-Holding Timing,
  OTHERWISE Label 1;
GEN.TARGET.ENV.LUNG.MATH.MODEL: Generation of Target Envelope for Lung Portrayal or Stylized Feedback through Mathematical Model
  GENERATE target-envelope outline for (initial) increment
  using the prescribed training objective to drive the mathematical model;
  ACCESS new constant lower-frequency bound (or other auditory variable such as word/phrase) for flow versus volume of time according to prescribed training;
  ACCESS new constant upper-frequency bound (or other auditory variable such as word/phrase) for flow versus volume of time according to prescribed training;

-continued

Presentation of Lung Portrayal or Stylized Feedback through Mathematical Model
  Begin:
    GENERATE (next) target-envelope target outline using GEN.TARGET.ENV.LUNG.MATH.MODEL
    DISPLAY (next) target-envelope outline;
    DISPLAY (next) trainee-generated visual-feedback outline as calculated by the mathematical model;
    DISPLAY (next) trainee-generated visual-feedback droplet distribution as calculated by the mathematical model;
    (Optionally) IF trainee-generated feedback outside target envelope THEN COLOR region between the two outlines AND (Optionally) OUTPUT tone or word/phrase auditory feedback;
    IF finished with inhalation THEN Presentation of Breath-Hold Timing,
    OTHERWISE Begin;
GEN.TARGET.ENV.LUNG.CEL.SELECT: Generation of Target Envelope for Lung Portrayal or Stylized Feedback through Cel Selection
  SELECT (initial) target-envelope outline or stylized-representation cel based on the prescribed training objective;
  ACCESS constant lower-frequency bound (or other auditory variable such as word/phrase) for flow versus volume of time according to prescribed training;
  ACCESS constant upper-frequency bound (or other auditory variable such as word/phrase) for flow versus volume of time according to prescribed training;
Presentation of Lung Portrayal or Stylized Feedback through Cel Selection
  Begin:
    SELECT (next) target-envelope target outline using GEN.TARGET.ENV.LUNG.CEL.SELECT;
    DISPLAY (next) target-envelope outline cel;
    COMPARE next trainee data value for volume to the data values of available outline or stylized-representation cels;
    SELECT closest outline or stylized-representation cel in value;
    DISPLAY (next) selected outline or stylized-representation cel;
    (Optionally) IF trainee-generated data value for volume outside that for outside target envelope THEN DISPLAY indicator of discrepancy (cel or generated graphic AND (Optionally) OUTPUT tone or word/phrase auditory output;
    CALCULATE a resultant trainee data value for aerosolized-medication droplet distribution given rate of inhalation to current time;
    SELECT closest droplet-distribution cel;
    DISPLAY (next) selected droplet-distribution cel;
    IF finished with inhalation THEN Presentation of Breath-Hold Timing,
    OTHERWISE Begin;

Description of Operation During test Maneuver

Following is a description of a cycle of operation of the apparatus. The procedure beings with test set up by the operator. Patient profile data such as name, age, height, sex, and ethnic background are entered by keyboard and stored in memory 126. (FIG. 1b). Alternatively, this data may be recalled from storage. Once the setup is complete the test maneuver involves the following steps:

1) An initial keyboard, mouse or other input signal is provided by the operator to the microprocessor 124. This signal sets the microprocessor 124 in the mode to start the test or training maneuver.

2) The patient is instructed to exhale fully or to functional residual volume as desired by the physician, and place the inhaler mouthpiece 102 in his mouth.

3) The operator then starts the training or test maneuver by directing the patient's attention to the display 126, and instructing the patient to begin inhaling and immediately thereafter actuate release of the medication. When the patient activates the inhaler the operator provides a second keyboard, mouse, or other input to the microprocessor 124. With this input the system begins recording flow data. Alternatively, the time of canister actuation can be detected by a microswitch 108 placed under the collar of the medication canister or by software recognition of a characteristic pressure spike generated at the time of medication release. Flow values are used to calculate volume values, and multiple values are stored in memory associated with each sample, including time, flow rate, and volume. The nature of feedback to the patient will depend upon the display format being used.

In the lung graphic format, medication is shown to enter the respiratory tract and move into the tracheobronchial tree is response to flow and cumulative volume measurements. In the x-y axes format, flow and volume values 420 are plotted in real time (less than twenty milliseconds) on the display axes 400 where the x axis represents cumulative volume and the y axis represents flow rate. It is noted that, while in the embodiment described here the x axis represents inspiratory volume between zero and seven liters and the y axis represents flow rate between zero and three liters per second, both the variables chosen for graphing and the scale of the axes could take a number of alternative forms. Such alternative parameters are possible and desirable as a result of differences in the characteristics of patients and aerosol medications involved, and preferences of the medical personnel performing the testing or training. The present invention is therefore not intended to be limited to the specific variables and axis scales illustrated herein.

4) The patient is prompted to continue to inhale slowly and steadily. Under the lung graphic feedback format, the patient will be instructed to inhale fast enough to move the medication down into the airways but slow enough to avoid its impaction or "sticking to" the sides of the throat and airways. Under the x-y format the patient is told to keep the moving line 420 in the colored target range 410, and to continue to inhale until the indicated volume is reached. FIGS. 4a, 4b, and 4c generally show the display 130 during the progression of this stage of the procedure.

5) At the point in time that the patient reaches a target or maximum inhaled volume, as evidenced by observation of the patient and/or a drop in the flow rate on the display, the operator instructs the patient to hold his breath. Also at this time the operator would provide a third keyboard or other input to the microprocessor 124. Alternatively, the cessation of flow at the end of inhalation can be recognized by the software and this input generated automatically. This third input causes the appearance of a timer 430, or alternative representation of time, on the display 126 which indicates the time passing from the time the input occurs. In the presently described embodiment, the microprocessor ceases to acquire flow data from the point of the third input. Thus from this point forward the patient may remove the inhaler 102 from his mouth (as he normally would do in routine usage of an inhaler).

6) The time display 430 continues to indicate the passage of time in seconds. During this time the operator encourages the patient to continue breath holding up to ten seconds (or some other duration if desired). The instruction to hold breath may also be conveyed by a display message which may flash on and off. During this stage the microprocessor 124 records in memory 126 the cumulative time since the third keyboard input. This measure represents the time elapsed during breath holding.

It will be appreciated that the parameter of the time period during which the breath is held is indicative of the amount of aerosol which would settle onto the lower airway surfaces by sedimentation. The time elapsed until exhalation is also determinative of the probable amount and distribution of aerosol medication deposited in the oropharynx.

7) At the point in time when the patient exhales, as observed by the operator, the operator provides a fourth keyboard or other input to the microprocessor 124 signifying the end of breath holding and the end of the maneuver. The timer 430 then disappears from the display. The microprocessor 124 performs several calculations on the data recorded during the maneuver, and sends the results to the display 126. If the display feedback used during the maneuver did not include the x-y type, a graph of the data collected is now presented in the x-y format. This curve provides an objective measure of the inhalation pattern for the operator.

8) The results of the test or training maneuver include, but are not limited to, an assessment of the degree of coordination of inhaler actuation with start of inhalation, the volume inhaled after actuation, the average inhalation rate, the volume inhaled at flow rates in the target range, and the duration of breath holding. Optionally, the display may also provide results in which the measured performance is compared with a desired goal. Some or all of the goals utilized may be patient-specific values. These goal values may be directly input to the program by the operator or calculated based upon patient-specific data. A single overall score assessing the relative success of the inhaler maneuver may also be provided.

9) A printout or electronic record is created to provide objective documentation of the patient's inhalation performance. Documentation of successive test maneuvers indicates the patient's capability to learn correct inhalation technique and retain this technique over time.

While the invention has been described in connection with what is presently considered to be the most practical and, preferred embodiments, it is to be understood that the invention is not limited to the disclosed embodiments, but on the contrary is intended to cover various modifications and equivalent arrangements within the spirit and scope of the appended claims.

What is claimed is:

1. An interactive inhaler training device for maximizing delivery of an airborne medication to a target site in a patient's lungs comprising:

an inhaler means including a source of airborne medication for inhalation by a patient;

a flow measurement means coupled with said inhaler means for measuring the flow of air through said inhaler means;

a microprocessor means coupled with said flow measurement means for producing a measure of flow as a function of inhaled volume;

storage means, coupled with said microprocessor means, for storing said flow and volume values and for storing additional parameters determining medication distribution to said target site;

display means, coupled with said microprocessor means for providing a visual display based on at least flow versus volume feedback to a patient for enabling a patient to maximize delivery of medication to said target site.

2. An apparatus according to claim 1 wherein said microprocessor means further includes means for recording the time of actuation of said inhaler means for calculating the timing of device actuation and means for recording the duration of inhalation and breath holding, and for applying said measured values to said storage means.

3. An apparatus according to claim 1 wherein said inhaler means includes a dry powder generator.

4. An apparatus according to claim 1 wherein said source of airborne medication comprises a pressurized canister of aerosol medication.

5. An apparatus according to claim 2 wherein said display means comprises means for superimposing said measured values of volume and flow simultaneously on an X-Y axis display to provide instantaneous visual feedback of a patient's inhalation.

6. An apparatus according to claim 5 wherein said display means comprises means for providing at least a two-dimensional portrayal of a patient's respiratory system and showing movement of medication into the patient's lungs in response to simultaneous flow and volume measurements of the patient's breathing.

7. An improved system for maximizing the delivery of an airborne medication, or the like to target sites in a patient's lungs, including airways and alveoli comprising:

inhaler means including a canister of airborne medication for delivery to the patient's lungs;

flow measuring means coupled with said inhaler means for measuring the flow of air through said inhaler means;

at least one microprocessor means coupled with said flow measurement means for recording measured values of flow and volume, including means for storing quantifiable parameters relating to patient lung function and for projecting patterns of medication deposition at the receptor sites within the patient's bronchial tree based on said parameters of lung function;

visual display means coupled with said microprocessor means for providing at least at two-dimensional graphic portrayal of the movement of said medication to the target sites.

8. An apparatus according to claim 7 wherein said graphic display means includes means for illustrating the deposition of said medication by means of sedimentation and diffusion in the airways and alveoli.

9. An apparatus according to claim 8 wherein said graphic display means includes means for illustrating expulsion of an inhaled substance in and out of the patient's lungs during inhalation expiration and breath holding.

10. An inhalation training system for facilitating maximized delivery of an airborne medication to receptor sites in a patient's lungs comprising:

inhaler means for providing a quantity of said medication or the like to a patient's lungs;

flow measurement means coupled with said inhaler means for measuring a patient's breathing through said inhaler;

microprocessor means responsive to said flow measurement means and including means for modulating quantifiable physiologic parameters indicative of a patient's lung function to provide a projected target envelope representative of maximized medication distribution in the lungs of a patient based on said physiologic parameters;

display means for displaying said projected target envelope including means for measuring a patient's actual breathing performance with said target envelope for providing an improved inhalation response to said patient.

11. a system according to claim 10 wherein said microprocessor means includes:

means for integrating the flow of air over time to produce a measure of the volume of air inhaled;

means for manipulating the values of quantifiable physiologic variables governing medication distribution in the lungs to produce a display of graphic images capable of conveying meaning and discrimination.

12. A system according to claim 11 wherein said quantifiable parameters include predicted lung volume and time flow rate values for a specific patient.

13. An apparatus according to claim 10 wherein said display means includes means for superimposing the measured values of the patient's inhalation simultaneously on the target envelope in order to provide visual feedback of the patient's breathing.

14. A system according to claim 13 wherein said display means includes means for providing at least two-dimensional graphic portrayal of the human lungs and bronchial tree with the lungs expanding or contracting in response to simultaneous flow and volume measurements of a patient's breathing.

15. An apparatus according to claim 13 wherein said display means includes means for providing a target envelope on an X-Y axis and for superimposing actual performance on sad target envelope.

16. A system according to claim 10 wherein display means includes means for generating a first set of graphic images capable of conveying meaning and discrimination with respect to a patient's projected inhalation and delivery pattern of medication to receptor sites in the patient's lungs; and means for generating a second set of graphic images capable of conveying meanings and discrimination, superimposed on said first set, which are representative of the patient's measured inhalation performance.

17. A system for training a patient in the use of an aerosol inhaler, or the like comprising:

an inhaler means containing a quantity of medication for application to a target site in a patient's lungs;

flow measurement means coupled with said inhaler means for providing an output signal representative of the flow of air into the patient's lungs upon inhalation from said inhaler means;

microprocessor means responsive to said output signal, including means for providing a measure of the volume of medication inhaled, said microprocessor means further comprising means for computing a projected delivery pattern of said medication to ad target site within the patient's lungs based upon measured parameters of the patient's inhalation and breath-hold maneuver;

storage means coupled with said microprocessor means for receiving a plurality of values representative of said measured parameters of the patient's inhalation and breath-hold maneuver;

display means coupled with said microprocessor means for providing a visual display of a projected pattern of medication distribution at the target site of the patient's lungs based upon said measured parameters of the patient's inhalation and breath-hold maneuver.

18. An apparatus according to claim 17 wherein said display means includes means for displaying an image representative of the diffusion and deposition of medication into a patient's airways and the distribution of said medication in and out of the patient's lungs during inhalation, expiration and breath holding.

19. An apparatus according to claim 17 wherein display means comprises a numerical score representing a rating of the likely level of success in delivering the desired dose of medication to the receptor sites in the respiratory tract, such as score of one to ten.

20. An apparatus according to claim 17 wherein said microprocessor, storage means coupled with said microprocessor, and display means are provided by a multimedia computer such as a video game apparatus.

21. An inhaler training device for maximizing the delivery of an airborne medication to receptor sites in a patient's lungs comprising:

an inhaler means including a source of airborne medication for inhalation by a patient;

a flow measurement means coupled with said inhaler means for measuring the flow of air through said inhaler means;

a microprocessor means coupled with said flow measurement means for integrating the flow of air over time to produce a measure of volume inhaled;

storage means, coupled with said microprocessor means, for storing said measured flow and volume values and for storing additional quantifiable diagnostic parameters relating to projected patterns of medication distribution to receptor sites in a patient's lungs;

a three dimensional display means for portrayal of a patient's lungs and airways and for showing the projected deposition of medication therein.

* * * * *

UNITED STATES PATENT AND TRADEMARK OFFICE
CERTIFICATE OF CORRECTION

PATENT NO. : 5,333,106

DATED : July 26, 1994

INVENTOR(S) : Ted W. Lanpher, at el

It is certified that error appears in the above-identified patent and that said Letters Patent is hereby corrected as shown below:

On the title page item [54] "POWER" should read --PROPER--
Column 1 line 3 "POWER" should read --PROPER--.

Signed and Sealed this

Eleventh Day of October, 1994

Attest:

BRUCE LEHMAN

*Attesting Officer*  *Commissioner of Patents and Trademarks*